(12) United States Patent
Kondo et al.

(10) Patent No.: US 8,865,969 B2
(45) Date of Patent: Oct. 21, 2014

(54) MUTANT PLANT, A METHOD FOR PRODUCING THEREOF AND A METHOD OF INCREASING FREQUENCY OF A GENETIC RECOMBINATION

(75) Inventors: Satoshi Kondo, Miyoshi (JP); Chikara Ohto, Toyota (JP); Kunihiro Ohta, Wako (JP); Shuichi Ohsato, Wako (JP); Norihiro Mitsukawa, Miyoshi (JP); Nobuhiko Muramoto, Gifu (JP); Hiroki Sugimoto, Aichi (JP)

(73) Assignees: Toyota Jidosha Kabushiki Kaisha, Aichi-ken (JP); Riken, Saitama (JP)

( * ) Notice: Subject to any disclaimer, the term of this patent is extended or adjusted under 35 U.S.C. 154(b) by 558 days.

(21) Appl. No.: 13/008,487

(22) Filed: Jan. 18, 2011

(65) Prior Publication Data

US 2011/0277189 A1    Nov. 10, 2011

(30) Foreign Application Priority Data

Jan. 15, 2010 (JP) .................................. 2010-007220
Jan. 13, 2011 (JP) .................................. 2011-004805

(51) Int. Cl.
 *C12N 15/87* (2006.01)
 *C12N 15/05* (2006.01)

(52) U.S. Cl.
USPC ........... 800/288; 800/293; 800/294; 435/469; 435/470

(58) Field of Classification Search
None
See application file for complete search history.

(56) References Cited

U.S. PATENT DOCUMENTS

| 6,037,162 A | 3/2000 | Raveh |
| 6,610,545 B2 | 8/2003 | Dujon et al. |
| 2008/0166809 A1 | 7/2008 | Ohta et al. |

FOREIGN PATENT DOCUMENTS

JP    4158920 B2    7/2008

OTHER PUBLICATIONS

Puchta et al 1996 PNAS 93: p. 5055-5060.*
Pingoud et al 2005 Cell Molecular Life Science 62: p. 685-707.*
Kanamaru et al 1999 Plant Cell Physiology 40:8 p. 832-842.*

* cited by examiner

*Primary Examiner* — Brent T Page
*Assistant Examiner* — Matthew Keogh
(74) *Attorney, Agent, or Firm* — Sughrue Mion, PLLC

(57) ABSTRACT

According to the present invention, a technique of increasing the frequency of genetic recombination in genomic DNA of a plant is established. Such technique comprises: introducing a restriction enzyme gene that can be expressed in a target plant cell into the plant cell and causing the restriction enzyme gene to be transiently expressed so as to induce genetic recombination of genomic DNA; or introducing a promoter and a restriction enzyme gene using the *Agrobacterium* method so as to induce genetic recombination of genomic DNA.

12 Claims, 13 Drawing Sheets
(8 of 13 Drawing Sheet(s) Filed in Color)

Bright field    Fluorescent filter

SEQUENCE LISTING

<160> NUMBER OF SEQ ID NOS: 26

<210> SEQ ID NO 1
<211> LENGTH: 30
<212> TYPE: DNA
<213> ORGANISM: Artificial Sequence

```
<220> FEATURE:
<223> OTHER INFORMATION: Synthetic DNA

<400> SEQUENCE: 1
gaggcgcgcc atggcccta cacaagccca                                30

<210> SEQ ID NO 2
<211> LENGTH: 30
<212> TYPE: DNA
<213> ORGANISM: Artificial Sequence
<220> FEATURE:
<223> OTHER INFORMATION: Synthetic DNA

<400> SEQUENCE: 2
gcttaattaa tcaatggtga tggtgatgat                                30

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
agacgataag cttgatatca                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
accggcaaca ggattcaatc                                           20

<210> SEQ ID NO 5
<211> LENGTH: 45
<212> TYPE: DNA
<213> ORGANISM: Artificial Sequence
<220> FEATURE:
<223> OTHER INFORMATION: Synthetic DNA

<400> SEQUENCE: 5 aggatcccg ggtggtcagt cccttatggc ccctacacaa gccca                45

<210> SEQ ID NO 6
<211> LENGTH: 31
<212> TYPE: DNA
<213> ORGANISM: Artificial Sequence
<220> FEATURE:
<223> OTHER INFORMATION: Synthetic DNA

<400> SEQUENCE: 6
agagctctgt acctcacggg ccggtgaggg c                              31

<210> SEQ ID NO 7
<211> LENGTH: 792
<212> TYPE: DNA
<213> ORGANISM: Artificial Sequence
<220> FEATURE:
<223> OTHER INFORMATION: Synthetic DNA

<400> SEQUENCE: 7 atggcccta cacaagccca gaaagtgctg gaagcttttg aggattttct gaagtgtttg    60
```

| | |
|---|---|
| gacctcgaga gctaccaaga aaaataccgc cccatcaaaa cagtagagca agacctacct | 120 |
| agagagctta acccacttcc agacttgtac gaccactatt ggaagcccaa cgggaacacc | 180 |
| cttcactttc cagattttga aactttcttc gaccagtggt gggagaagcg cctccggccc | 240 |
| ctaaacgagt ttattcgcaa gtattttggg ggatgttcct atgaatttgt ccgtctcggc | 300 |
| ttagaagcga ggctctaccg gaccgctgtt tccatttgga cgcaatttca cttttgctat | 360 |
| cgctggaacg cctcttgtca acttcgcttg acggccacct gggagttgga cgcccagggg | 420 |
| atagatgcac aaattcaagc agaagaccgc ctgataggca ttcagataaa aaggaaacc | 480 |
| tatcgctcgg aagcccggga gggaaaccgc ttcctaagaa ggcgcgaaca ttccgccctc | 540 |
| ctggaagttc cctacacgct gcaaagccca gaggaactcg aaagaaaagc ccagcgtgcc | 600 |
| cgaaccagag aagaagccta ccgcttgtgg gtcaaaatcg cccaccatct agaacggctt | 660 |
| cccaacggat tcgtcatctt ccgagaaagc tacgtaaagg acttggaaaa cttttttaaag | 720 |
| caaaacgcca ctacattgtc cggactcata ccctgggata aggtagcccg ggaagccctc | 780 |
| accggcccgt ga | 792 |

<210> SEQ ID NO 8
<211> LENGTH: 74
<212> TYPE: DNA
<213> ORGANISM: Artificial Sequence
<220> FEATURE:
<223> OTHER INFORMATION: Synthetic DNA

<400> SEQUENCE: 8

| | |
|---|---|
| agagctcccc gggctatcct ccaacctttc tcttcttctt aggctgcaga cctcccgggc | 60 |
| cggtgagggc ttcc | 74 |

<210> SEQ ID NO 9
<211> LENGTH: 831
<212> TYPE: DNA
<213> ORGANISM: Artificial Sequence
<220> FEATURE:
<223> OTHER INFORMATION: Synthetic DNA

<400> SEQUENCE: 9

| | |
|---|---|
| atggcccta cacaagccca gaaagtgctg gaagcttttg aggattttct gaagtgtttg | 60 |
| gacctcgaga gctaccaaga aaaataccgc cccatcaaaa cagtagagca agacctacct | 120 |
| agagagctta acccacttcc agacttgtac gaccactatt ggaagcccaa cgggaacacc | 180 |
| cttcactttc cagattttga aactttcttc gaccagtggt gggagaagcg cctccggccc | 240 |
| ctaaacgagt ttattcgcaa gtattttggg ggatgttcct atgaatttgt ccgtctcggc | 300 |
| ttagaagcga ggctctaccg gaccgctgtt tccatttgga cgcaatttca cttttgctat | 360 |
| cgctggaacg cctcttgtca acttcgcttg acggccacct gggagttgga cgcccagggg | 420 |
| atagatgcac aaattcaagc agaagaccgc ctgataggca ttcagataaa aaggaaacc | 480 |
| tatcgctcgg aagcccggga gggaaaccgc ttcctaagaa ggcgcgaaca ttccgccctc | 540 |
| ctggaagttc cctacacgct gcaaagccca gaggaactcg aaagaaaagc ccagcgtgcc | 600 |
| cgaaccagag aagaagccta ccgcttgtgg gtcaaaatcg cccaccatct agaacggctt | 660 |
| cccaacggat tcgtcatctt ccgagaaagc tacgtaaagg acttggaaaa cttttttaaag | 720 |
| caaaacgcca ctacattgtc cggactcata ccctgggata aggtagcccg ggaagccctc | 780 |
| accggcccgg gaggtctgca gcctaagaag aagagaaagg ttggaggata g | 831 |

```
<210> SEQ ID NO 10
<211> LENGTH: 27
<212> TYPE: DNA
<213> ORGANISM: Artificial Sequence
<220> FEATURE:
<223> OTHER INFORMATION: Synthetic DNA

<400> SEQUENCE: 10
agtcgactct ggtggtttca acttggg                                         27

<210> SEQ ID NO 11
<211> LENGTH: 27
<212> TYPE: DNA
<213> ORGANISM: Artificial Sequence
<220> FEATURE:
<223> OTHER INFORMATION: Synthetic DNA

<400> SEQUENCE: 11
aggatcctgt tcgttgcttt tcgggag                                         27

<210> SEQ ID NO 12
<211> LENGTH: 2187
<212> TYPE: DNA
<213> ORGANISM: Artificial Sequence
<220> FEATURE:
<223> OTHER INFORMATION: Synthetic DNA

<400> SEQUENCE: 12
tctggtggtt tcaacttggg agcaacatat tcatcacatc gtccacaaca acagccacaa      60
catacttcat ctgtgagtgg cagtctctcc tatccctata tgtatacaag ccggaacttt     120
cttcaatttg catatctcat attattatgg tactgcatca tgtggttggg ccacacttgc     180
tccaactacc gtatcttatc atttaattct tatttaatac cagactggtg ggctacaggg     240
tcttggcctt agacctctaa gctcgcctaa tgcagtttcc agtattggtt atgatcagct     300
tattcagcag tatcagcaac atcaaaatca atcccagttc cctgtgcaac agatgtcatc     360
aatcaaccaa tttagagatt ctgagatgaa atcgacacag tcagaggcag atccttttg      420 cttgcttggc ttgttagacg tactaaacag gagcaaccct gaattgacct cacttgctct     480
tggcatcgac ttgacgacgc taggattgga tttgaattca actggaaatc tctacaagac     540
atttgcgtct ccttggacaa atgaaccggc aaagagcgag gtcgagttca cagtaccaaa     600
ttgttactac gccacagaac ctccgcctct aactgtaagt tccctctgtt gttgcgagta     660
gtaccaacaa gtatttcct cgattttgtt aacaaatgtg tcattatttc cgtttgttgc      720
agcgagctag tttcaaaagg ttctcctacg agttattgtt ctacacattt tacaggtctg     780
ttattagatc agcattcagc gtcacatttg cccaactcct aaattaacct tgggctttta     840
aacttattac tttgctctaa ttattgttcc agtatgccaa aagatgaagc acagctgtac     900
gcagcagatg aactgtatgt ttttctcta ctgtaatctt tgatctattc gtttactccg      960
ctctctttgg ctgagacttt tgagttcgat tgacatgttg cagttacgaa agaggttggt    1020
tttaccacaa ggaactcaga gtatggttct tcagagtcgg ggaacctta gtcagggcag     1080 ctacatatga agaggaaca tacgaatacc ttgatccaaa ttcgttcaaa acagtgagaa     1140
aggtaagccg acgattattg caggaatatc tatttccttg ttctcgaatt tgcagtgtta    1200
tgagtgaatt tgctggtga tggttatcgc aggaacattt tgttatcaag tacgagctta     1260
tggaaaagag accaagcttg ctgcagcttt gacgacaagt aggtttgttc aattagtagc    1320
atctttacaa tgtaaagctt ttctcttcat ttctctttct ttctttcttt catgcaagtt    1380
```

```
ctattgatta gaaaccaaaa ccatgacata tcacattttc aattttttaac cccaagtttc    1440 ccaaaaaggt aatcacaatt actttccatg gtcatttctt ctggttcaag catgacatga    1500
acaggcaata aataagttga gattttgatc acagtaactg atacttgaat cgaatcattt    1560
agattttttt tttttttagt ttacttgttt agtaaatatg ttgtctatgt ttgtcacaaa    1620
aacgtggctc agttcttgta tatatggaga caaaaaaatc cattaaaaga ttgttgacat    1680
tctcggaaat ttagtgccaa ctgttattgc gagaacttac tatagttttc ctttggcgaa    1740
aagctaataa tcttaaatct tgattttgtc ctcttttctc tgagttagat tttcttaaat    1800
tccacttccg acctattaag aaatgggctt ttgcaaagaa gatccgcttc actgagcccg    1860
tatctcgaag aggataatac aacaacaaag caaaacggca cgtagtttta attgtaacca    1920
aggattgcat ttcggtcttg tttcaacaaa cgaaacttcc tgaaatgcca agaaaaatct    1980
ggtcatttca ccacagtgat cattgtgtat gtgttctaaa gactccaagc gaaggtttta    2040
gaaaaaggag cattttctat tctattcaag aaactcgaag aacattctct cttcatcctc    2100
taacttccct ataaatatgt cctttgctaa tcagatcaaa tcagcaggaa aatcaagaac    2160
caaaagtctc ccgaaaagca acgaaca                                        2187

<210> SEQ ID NO 13
<211> LENGTH: 28
<212> TYPE: DNA
<213> ORGANISM: Artificial Sequence
<220> FEATURE:
<223> OTHER INFORMATION: Synthetic DNA

<400> SEQUENCE: 13
agtcgaccga tctttctcca acaagctt                                         28

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA

<400> SEQUENCE: 14
aggatccgct cgttcttagc ctatattcg                                        29

<210> SEQ ID NO 15
<211> LENGTH: 2153
<212> TYPE: DNA
<213> ORGANISM: Artificial Sequence
<220> FEATURE:
<223> OTHER INFORMATION: Synthetic DNA

<400> SEQUENCE: 15
cgatctttct ccaacaagct tgaatcgatt taccctttaaa attccagctt ctctctatgt     60
atctcatcca acaagatgca gcatttcaaa cccgtcgagc tctgaggaat tgttgaattc    120
caatggtgga atgtctaggg catcgattag tgtcttcgga ggtacttccc ttaacaatct    180
caagatgcaa gtgggcagtc caatttctct gcattcaatc aatccattag caaagctgag    240
tttgagtgat caggcatttc ttctcttggc cttcatcgtt tgcacggtaa aaggagtttg    300
ctcgtgtttt gttttgacca ttttttgttga ttcattgata aggtttaga cttttgatc    360 tcttttgatg gtcctctgtt acagacttca gtggctttta caagtcttgt gattacagct    420
attcctacac ttgtggtaag tctccacatt tgtctcaatt cttttgcttc agctatatcc    480
taaccgcatc actaattta aaactgtttc aagtcattac caatgaatca acaaaaatgg    540
```

```
tcaaaacaga tgaacaaaga attgattatt tgtaatatgc tatcaacaat ctgacatata    600
cctttcaaa ctcagtgaga aactatgaca tgatctatgt tatgagtgta gtcctctgct    660
tgaaatttct actccacact tgctgttagc accaactgaa aggataaaag gctaatgagt    720
aacacatgag tacagtcact aacagataaa agattgaact ataattgttg aattccacac    780
ttgactcttc tttatatgtg tcctagattt ggttcagcta tatgatcatt tctattttg    840
gatttggctg aattcaacaa agcttggtgg aattttcag tttaatatgt ctgtctcttt    900
gttcttggat tgatatctat tcagtatgtc ctatatttac ttacacacct tcaggccatg    960
ggtagagctg caacttcctt tgcaaagtta gctgacacag ctcgcaaaga actccctagt   1020
acattggcag cggtaaggct ctctggcatg gaaataagcg atcttactct tgaattgagc   1080
gatttaaggt tatctctaaa gctctttct tttcttttct tttctggctt ttgatcatct   1140
caactctaaa aaagtgaat gctacatgtt tcaaagcaat tagttcacaa ttagttcttc    1200
cgagtcacct tgttatctgt ccggaataag aaacttttc taaatcatta ttatgcgatg   1260
caaatggttt cagccaagat ataacagatg ggataaacaa atcagctaaa gcggttcaag   1320
cagctgaagc tggaatcaaa cagattggaa cacttgcaca gcagcaaact ctctgtaagc   1380
ttcttctaag cttttggata atctgtaata aaagctgctg ttcatggtgg caacagttca   1440
cactggtaaa aaaaagcgg aaaatatgat ctgatgatga acttgatctt gtgattcagc   1500
aatgattgaa gagagagcaa atttaccaga aatatcacta caacctgttg tggctggtgc   1560
agccgaaaag acttctcacg caatcggcag tgcaaccaag agactaatga acattataac   1620
cggaggaaac aaggatgaag attagacatt tagaagtttt cacttggagt gtgtttttgg   1680
tccgtctttg tttgaaggga ttagtacaag gtaaagtcca tttagggaaa cagagaatct   1740
atgaacaaga agacttttta gtaaaatttg gtatattat gaaacctgaa gtgtaactgt   1800
gtaagacaca aaagaagaaa taataacagc cacagccatt ttaagatgta caacagcaga   1860
taaaatagtt tacataacaa gccgacaaaa aaaaaaaact attctattct tacatatggg   1920
ttgactttgc aaagatggta atagtgtgat tgggattggg ccaaagttaa taggcccaaa   1980
agaagtggaa aattagaagt aatgaatcct ttgattgaga tagaagcttt atcctcttct   2040
tcgtcttcat catccgcgca tcaccagttt ttctctctc tctacaaatc ttcttaacgg   2100
cctttcatca atggtcagca gacttagctt tcgaatatag gctaagaacg agc          2153
```

```
<210> SEQ ID NO 16
<211> LENGTH: 40
<212> TYPE: DNA
<213> ORGANISM: Artificial Sequence
<220> FEATURE:
<223> OTHER INFORMATION: Synthetic DNA

<400> SEQUENCE: 16
agcttggcgc gccttaatta aactagtctc gaggtcgact                           40

<210> SEQ ID NO 17
<211> LENGTH: 40
<212> TYPE: DNA
<213> ORGANISM: Artificial Sequence
<220> FEATURE:
<223> OTHER INFORMATION: Synthetic DNA

<400> SEQUENCE: 17
ctagagtcga cctcgagact agtttaatta aggcgcgcca                           40
```

<210> SEQ ID NO 18
<211> LENGTH: 537
<212> TYPE: DNA
<213> ORGANISM: Sporosarcina sp.

<400> SEQUENCE: 18

| | | |
|---|---|---|
| atgggcatga acagcagatt gttaagccag cgggctagac agccaggcca tgaccagacc | 60 |
| ttcagagaat cggaaagcaa ctttgtagag gctcttgaga tgattctaga tcctgacgag | 120 |
| tggcgggttg aggatcaccc gcctgagttg agacgtatta taggcggcag atatggcgtt | 180 |
| gttccggaag cttctataga atatcttccg acaggccgaa agttttttt tgaagtgaag | 240 |
| aaacagggcc ctgcgggcaa cgcggatgaa agagcttgta agcaccatac agtgcagttc | 300 |
| tacaaggagc tgcatgcact atttggctac gattatcatc cattcgctac cattatgtgt | 360 |
| gaatcattgg caactctcga agatatact gttaagcatc cttttactt tgaggagggc | 420 |
| cattactttt gctgggttga ttacgacgtt gaccttcttg ctgactttat tgctcagatt | 480 |
| gcgtctagat ggcttatgga tccaactgca gaacctcccc aagcactccc tcaataa | 537 |

<210> SEQ ID NO 19
<211> LENGTH: 35
<212> TYPE: DNA
<213> ORGANISM: Artificial Sequence
<220> FEATURE:
<223> OTHER INFORMATION: Synthetic DNA

<400> SEQUENCE: 19
gaggcgcgcc atgggcatga acagcagatt gttaa                35

<210> SEQ ID NO 20
<211> LENGTH: 35
<212> TYPE: DNA
<213> ORGANISM: Artificial Sequence
<220> FEATURE:
<223> OTHER INFORMATION: Synthetic DNA

<400> SEQUENCE: 20
gcttaattaa ttattgaggg agtgcttggg gaggt                35

<210> SEQ ID NO 21
<211> LENGTH: 990
<212> TYPE: DNA
<213> ORGANISM: Sporosarcina sp.

<400> SEQUENCE: 21

| | | |
|---|---|---|
| atggccgaat ggaacgtttg gacgcagaga agtgttgagc tgctggagaa aggatatttg | 60 |
| gacaaattgc tccaagtgta caaaggagaa tcaggtagtt ctagaagtgt tccagaggaa | 120 |
| gtcgaagaga agcttaggga ggcttataag gcctatgaag gtagacagga ttctcccgaa | 180 |
| gcagaaacaa agcttgttga ggctgttttg aacgcaagaa aaaaggtcga aggagcccct | 240 |
| ttcaatcatc cttatcttcc tcttgtctat tatcttgtgt ctgaaaaagc cgaaaaggct | 300 |
| aacaaagcac ttgaggaggc gttgcaggaa gttgcttcta acatccaga actataaga | 360 |
| gttctcgcta aggaggctca aggaggggga gtggaggcgc tgattcagcg actcaaggaa | 420 |
| cccccctgaga ttaacagaca gatcggaccg atgttcaaaa ggtggtataa ggaggaactt | 480 |
| aagggaaaga ttgaagagag actgccagga ccaactaaac caagatagt tgttgtttca | 540 |
| cctgagaaat ccaaaccgga acaggctccg cttattgcag agaggaggc tggtattatt | 600 |
| atttataccg gatcggacga agctctcaag gatgcggcca agaaaaacct tggattgggt | 660 |

```
gaagaagcgg aattagggac taagggcgtg gatttttacg tagtgatccg aagaagtcct      720
gaagaaactt ggcatttaac tggagaggtg aagtttcaga gtgattttgg tggtaaccag      780
gataatcaga aactggtagc taaggcatct attagactcg atttagagaa gcgacacata      840
ggtattgttg tggtagatgg tatgccggtt gtgtctaagt tcagaggatg ggctggactc      900
ggaaaggaaa caattgttac tagtgttctt ttgcttcctg atcttatcgc tgagctatat      960
caaaagggag aggaagccct tggtctgtaa                                       990
```

<210> SEQ ID NO 22
<211> LENGTH: 35
<212> TYPE: DNA
<213> ORGANISM: Artificial Sequence
<220> FEATURE:
<223> OTHER INFORMATION: Synthetic DNA

<400> SEQUENCE: 22

```
gaggcgcgcc atggccgaat ggaacgtttg gacgc                                 35
```

<210> SEQ ID NO 23
<211> LENGTH: 35
<212> TYPE: DNA
<213> ORGANISM: Artificial Sequence
<220> FEATURE:
<223> OTHER INFORMATION: Synthetic DNA

<400> SEQUENCE: 23

```
gcttaattaa ttacagacca agggcttcct ctccc                                 35
```

<210> SEQ ID NO 24
<211> LENGTH: 21
<212> TYPE: DNA
<213> ORGANISM: Artificial Sequence
<220> FEATURE:
<223> OTHER INFORMATION: Synthetic DNA

<400> SEQUENCE: 24

```
aggtgaagtt ccagagtgat t                                                21
```

<210> SEQ ID NO 25
<211> LENGTH: 21
<212> TYPE: DNA
<213> ORGANISM: Artificial Sequence
<220> FEATURE:
<223> OTHER INFORMATION: Synthetic DNA

<400> SEQUENCE: 25

```
aatcactctg gaacttcacc t                                                21
```

<210> SEQ ID NO 26
<211> LENGTH: 18
<212> TYPE: DNA
<213> ORGANISM: Artificial Sequence
<220> FEATURE:
<223> OTHER INFORMATION: Synthetic DNA

<400> SEQUENCE: 26

```
gggctccacg tggccggc                                                    18
```

MUTANT PLANT, A METHOD FOR PRODUCING THEREOF AND A METHOD OF INCREASING FREQUENCY OF A GENETIC RECOMBINATION

BACKGROUND OF THE INVENTION

1. Field of the Invention

The present invention relates to a mutant plant produced by inducing genetic recombination of genomic DNA, a method for producing a mutant plant, and a method of increasing the frequency of genetic recombination.

2. Background Art

There is a known method for obtaining a variety of mutants by artificially inducing genetic recombination of genomic DNA (JP Patent No. 4158920). According to this method, so-called "genomic shuffling" is artificially induced. Thus, a mutant having rearranged genomic DNA can be efficiently obtained.

The method described in JP Patent No. 4158920 is a method of increasing the frequency of genetic recombination by causing TaqI (a restriction enzyme that recognizes 4 nucleotides) to be expressed in target fungal cells, transiently activating TaqI through temperature control, and introducing at least two double strand breaks at arbitrary sites in genomic DNA. Fungal cells having improved genetic characteristics can be produced by this method.

Specifically, in the method disclosed in JP Patent No. 4158920, first, the TaqI gene is transformed into yeast with an auxotrophic marker. A transformed yeast is obtained based on auxotrophy. Next, the transformed yeast is retained for a certain time period at a temperature at which TaqI is activated (50° C.) such that TaqI is transiently activated. It has been shown that such temperature treatment causes increased frequency of genetic recombination.

In addition, JP Patent No. 4158920 teaches that the above method can be applied to plant cells (paragraph 0011). However, JP Patent No. 4158920 does not disclose the Example in which the method was actually applied to plant cells. Therefore, it is still unknown whether mutant plants can be produced by applying the method to plant cells.

SUMMARY OF THE INVENTION

The use of the method disclosed in JP Patent No. 4158920 for plant cells resulted in the death of the plant cells. Therefore, it was impossible to obtain mutant plants having rearranged genomic DNAs. Therefore, an object of the present invention is to provide mutant plants having different characteristics, a method for producing such mutant plants, and a method of increasing the frequency of genetic recombination in a plant by establishing a technique of increasing the frequency of genetic recombination in genomic DNA of a plant.

As a result of intensive studies in view of the above circumstances, the present inventors found that a variety of mutant plants can be obtained by increasing the frequency of genetic recombination in plant genomic DNA via induction of transient expression of a restriction enzyme gene or introduction of a restriction enzyme gene by the *Agrobacterium* method. This has led to the completion of the present invention.

The present invention encompasses the following.

Specifically, the method for producing a mutant plant of the present invention is a method for producing a mutant plant by introducing a restriction enzyme gene that can be expressed in a target plant cell into a target plant cell and causing the transient expression of the restriction enzyme gene so as to induce genetic recombination of genomic DNA. In addition, the method of increasing the frequency of genetic recombination of the present invention is a method comprising introducing a restriction enzyme gene that can be expressed in a target plant cell into a target plant cell and causing the transient expression of the restriction enzyme gene so as to induce genetic recombination of genomic DNA.

In the present invention, it is particularly preferable to introduce a restriction enzyme gene into the above plant cell by a particle gun method. With the use of a particle gun method, a nucleic acid construct (e.g., a vector such as a plasmid) that contains a restriction enzyme gene can be physically-introduced into a plant cell. In such case, it is preferable to culture the plant cell in a medium to which selection pressure corresponding to a selection marker has not been applied, following treatment for introducing the restriction enzyme gene into the plant cell. In a conventional transformation method, an individual plant in which a desired gene is stably present is selected by continuously applying selection pressure corresponding to a selection marker that has been introduced along with the gene. Then, the plant is continuously grown with the application of selection pressure. However, according to the present invention, a plant is continuously grown under selection-pressure-free conditions, making it possible to cause the transient expression of the restriction enzyme gene.

In the present invention, it is preferable to use, as the above restriction enzyme gene, a thermophile-derived restriction enzyme gene and to maintain temperature below the level at which a restriction enzyme encoded by the gene is activated. Thermophile-derived restriction enzymes are activated at 40° C. to 50° C. in yeast. Therefore, it is essential for the method disclosed in JP Patent No. 4158920 to comprise a step of incubation at such temperature range. In contrast, the method of the present invention does not comprise a step of incubation at such temperature range, resulting in significant inhibition of restriction enzyme activity.

However, according to the present invention, it is also possible to physically-introduce, as the above restriction enzyme gene, a thermophile-derived restriction enzyme gene into a plant cell, treat the cell at a temperature of approximately 40° C. to 60° C. at which restriction enzyme activation is achieved, and culture the plant cell while maintaining a temperature below the temperature range. During the treatment of the plant cell at the above temperature, restriction enzyme activity can be enhanced. In addition, since temperature is maintained below the above temperature range during plant cell culture, restriction enzyme activity can be significantly inhibited during culture.

Meanwhile, a method for producing a mutant plant of the present invention is a method for producing a mutant plant by introducing a promoter and a restriction enzyme gene by the *Agrobacterium* method so as to induce genetic recombination of genomic DNA. Further, the method of increasing the frequency of genetic recombination of the present invention is a method comprising introducing a promoter and a restriction enzyme gene by the *Agrobacterium* method for the transient expression of the restriction enzyme gene so as to induce genetic recombination of genomic DNA.

Here, as a promoter that controls restriction enzyme gene expression, a cauliflower-mosaic-virus-derived 35S promoter or a promoter having a promoter activity lower than that of a cauliflower-mosaic-virus-derived 35S promoter are preferably used. An example of a promoter having a promoter activity lower than that of the cauliflower-mosaic-virus-derived 35S promoter is a promoter for a gene encoding the *Arabidopsis* sigma factor (AtSIG2).

Meanwhile, the present invention encompasses a mutant plant produced by the method for producing a mutant plant described above. The mutant plant of the present invention is structured in such a way that genomic DNA is rearranged via genetic recombination so as to exhibit a variety of genetic characteristics.

Effects of the Invention

According to the present invention, the proportion of plant cells killed by a restriction enzyme gene introduced therein can be reduced. Therefore, a mutant plant having genomic DNA rearranged via genetic recombination can be produced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENTS

Figure 1:
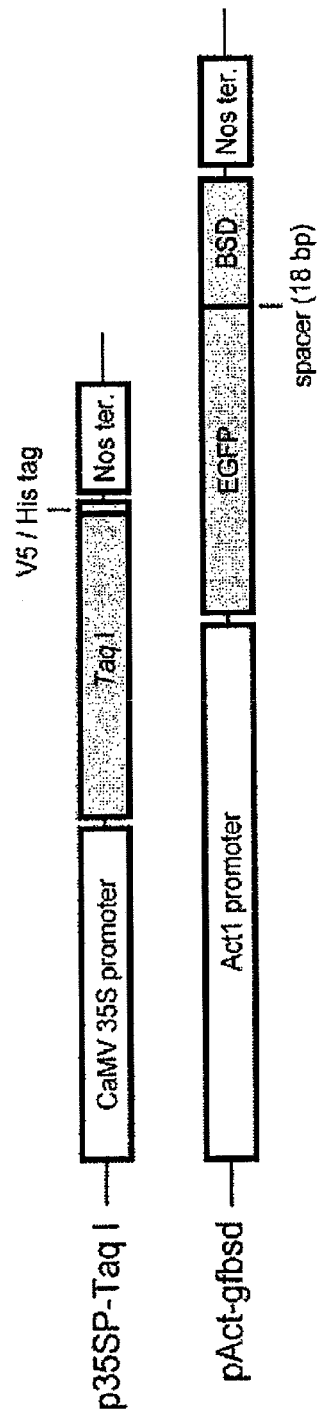
FIG. 1 schematically shows the constructs of the plasmids used in Comparative Example 1.

Hereinafter, the present invention is described in more detail.

The method for producing a mutant plant of the present invention is a method for producing a mutant plant having rearranged genomic DNA in which the frequency of genetic recombination of genomic DNA has been increased by inducing the transient expression of a restriction enzyme gene in a plant cell or introducing a restriction enzyme gene into a plant cell by the *Agrobacterium* method.

1. Cells

Plant cells of any type can be used in the present invention as long as they are plant cells in which genetic recombination has taken place, even if at low levels. Persons skilled in the art can readily select such cells.

The term "genetic recombination" used herein has a broad meaning indicating a phenomenon of DNA cleavage/rejoining involving DNAs. The meaning of the term "genetic recombination" used in the present invention encompasses homologous recombination, non-homologous recombination, gene conversion, inversion, unequal crossover, crossover, translocation, copy number change, chromosome fusion, and mutation. In addition, the term "rearrangement" refers to a situation in which the increased frequency of "genetic recombination" causes a recombination between existing genomic sequences, resulting in partial or complete alteration of the genomic sequence.

Examples of target plants (i.e., base plants for mutant plants) include, but are not limited to, dicotyledons and monocotyledons, such as plants belonging to the families Brassicaceae, Gramineae, Solanaceae, Leguminosae, Salicaceae, and the like (see below).

Family Brassicaceae: thale-cress (*Arabidopsis thaliana*), rapeseed (*Brassica rapa, Brassica napus*), cabbage (*Brassica oleracea* var. *capitata*), napa (*Brassica rapa* var. *pekinensis*), ging-geng-cai (*Brassica rapa* var. *chinensis*), turnip (*Brassica rapa* var. *rapa*), turnip greens (*Brassica rapa* var. *hakabura*), potherb mustard (*Brassica rapa* var. *lancinifolia*), komatsuna (*Brassica rapa* var. *peruviridis*), pak Choi (*Brassica rapa* var. *chinensis*), daikon (*Brassica Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), wisteria (*Wisteria floribunda*), peanuts (*Arachis hypogaea*), bird's foot trefoil (*Lotus corniculatus* var. *japonicus*), common bean (*Phaseolus vulgaris*), azuki bean (*Vigna angularis*), Acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), wax palm (*Copernicia*), and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.

Family Caryophyllaceae: carnation (*Dianthus caryophyllus*) and the like.

Family Salicaceae: poplar (*Populus trichocarpa, Populus nigra,* or *Populus tremula*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus virgatum*), sorghum (*Sorghum*), switch grass (*Panicum*), and the like.

Family Liliaceae: tulip (*Tulipa*), lily (*Lilium*), and the like.

Family Myrtaceae: eucalyptus (*Eucalyptus camaldulensis, Eucalyptus grandis*), and the like.

Plant cells used in the present invention are cultured under conditions used in known methods in the art. Needless to say, culture is carried out using a medium appropriate for selected cells under appropriate culture conditions (e.g., culture temperature). As such medium, a conventionally known medium used for plant cell culture or tissue culture can be used.

2. Restriction Enzyme

A restriction enzyme gene to be introduced into a target plant cell is not particularly limited. Examples thereof include genes encoding TaqI, TspRI, Tsp45I, Sse9I, MseI, DnpI, and CviAII.

Specifically, any restriction enzyme gene can be used as long as it encodes a restriction enzyme that allows introduction of DNA double strand breaks at given sequence sites in the genomic DNA of a plant cell. In addition, since the increase rate of frequency of genetic recombination depends on the number of sites cleaved by a restriction enzyme in genomic DNA, it is preferable to use a restriction enzyme in which a recognition sequence is present at an adequate existing probability. For example, such restriction enzyme is preferably a restriction enzyme recognizing a sequence comprising 4 to 6 nucleotides, more preferably a restriction enzyme recognizing a sequence comprising 4 to 5 nucleotides, and most preferably a restriction enzyme recognizing a sequence comprising 4 nucleotides.

In addition, it is preferable to use, as a restriction enzyme, a restriction enzyme that is activated under conditions differing from plant cell culture conditions. "Conditions differing from ordinary culture conditions" may be arbitrarily determined as long as they can be selected by persons skilled in the art. However, for example, conditions for adding a substance (e.g., metal ions) necessary for activation of a restriction enzyme to be used or temperature conditions necessary for activation of a restriction enzyme can be used. It is particularly preferable to use, as a restriction enzyme, a thermophile-derived restriction enzyme, the optimum temperature for which falls within a high temperature range above the culture temperature for plant cells. For example, the optimum temperature for TaqI and Tsp45I is 65° C., and the optimum temperature for Sse9I is 55° C.

As described above, if a restriction enzyme that is activated under conditions differing from plant cell culture conditions is used, it is possible to determine whether to cause the restriction enzyme to be active under such conditions or to cause the restriction enzyme to be less active under conditions other than such conditions after causing the restriction enzyme gene to be expressed in a plant cell. For instance, if a restriction enzyme is expressed in plant cells and the plant cells die due to the excessively high level of activity of the restriction enzyme, it is possible to maintain the restriction enzyme at a lower level of activity under conditions other than the above conditions so as to avoid the death of the plant cells.

For instance, if TaqI is expressed as a restriction enzyme in plant cells, high-activity TaqI can be realized as a result of incubation at 40° C. to 60° C. and preferably at 40° C. for 1 to 30 minutes. In addition, when TaqI is expressed in plant cells and the cells are continuously cultured at less than 40° C., low-activity TaqI can be realized.

Meanwhile, when the restriction enzyme gene is introduced into a plant cell by a transformation method described below in detail, a nucleic acid construct that allows the expression of the gene is introduced into the plant cell. The term "nucleic acid construct" used herein refers to, for example, an expression vector comprising a promoter that allows the gene expression in a plant and the restriction enzyme gene. As a vector serving as a basis of the expression vector, a variety of conventionally known vectors can be used. For example, plasmids, phages, cosmids, and the like can be used, and they can be appropriately selected depending on the plant cells used for gene expression and gene introduction methods. Specific examples of such vectors include pBR322, pBR325, pUC19, pUC119, pBluescript, pBluescriptSK, and pBI vectors. In particular, when *Agrobacterium* is used for a method for introducing a vector into a plant, a pBI binary vector is preferably used. Specific examples of such pBI binary vector include pBIG, pBIN19, pBI101, pBI121, and pBI221.

A promoter to be used herein is not particularly limited, as long as it allows the expression of a restriction enzyme gene in a plant. Any known promoter can be appropriately used. Examples of such promoter include a cauliflower mosaic virus 35S promoter (CaMV35S), a different actin gene promoter, a different ubiquitin gene promoter, a nopaline synthase gene promoter, a tobacco PR1a gene promoter, a tomato ribulose 1,5-bisphosphate carboxylase oxidase small subunit gene promoter, and a napin gene promoter.

In addition, an expression vector may further contain additional DNA segments other than a promoter and the above restriction enzyme gene. Examples of such additional DNA segments include, but are not particularly limited to, a terminator, a selection marker, an enhancer, and a nucleotide sequence for enhancing translation efficiency. Also, the above recombinant expression vector may further have a T-DNA region. A T-DNA region can enhance efficiency of gene introduction particularly when the above recombinant expression vector is introduced into a plant using *Agrobacterium*.

A transcription terminator is not particularly limited as long as it functions as a transcription termination site. A known transcription terminator can be used. Specifically, for example, a transcription termination region (Nos terminator) of a nopaline synthase gene, a transcription termination region of a cauliflower mosaic virus 35S (CaMV35S terminator), or the like can be preferably used. Of these, the Nos terminator is more preferably used. In the case of the above recombinant vector, it is possible to prevent synthesis of an unnecessarily lengthy transcript after introduction of the vector into a plant cell by arranging a transcription terminator at an appropriate position.

For example, as a selection marker, a drug resistance gene can be used. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence used for increasing translation efficiency is an omega sequence from tobacco mosaic virus. This omega sequence is arranged in an untranslated region (5'UTR) of a promoter so that the translation efficiency of the fusion gene can be increased. Thus, the recombinant expression vector may contain various DNA segments depending on purpose.

A method for constructing an expression vector is not particularly limited. A promoter, a restriction enzyme gene, and, if necessary, an additional DNA segment may be introduced in a predetermined order into an appropriately selected vector serving as a basis. For example, a restriction enzyme gene and a promoter (and, if necessary, a transcription terminator or the like) are ligated to construct an expression cassette and then the cassette may be introduced into a vector. Upon construction of an expression cassette, DNA segments are prepared to have protruding ends (complementary to each other) at their cleavage sites, and they are allowed to react with each other with the use of a ligation enzyme. Thus, the order of the DNA segments can be specified. In addition, when an expression cassette contains a terminator, DNA segments may be arranged, from upstream, in the order of a promoter, a restriction enzyme gene, and a terminator. Also, the type of reagent used for expression vector construction (i.e., a restriction enzyme, ligation enzymes, or the like) is not particularly limited. Commercially available reagents can be appropriately selected and used.

3. Transformation

According to the present invention, the above restriction enzyme gene is transiently expressed in a plant cell or it is introduced into a plant cell by the *Agrobacterium* method. In either case, the frequency of genetic recombination of genomic DNA can be increased without causing the death of plant cells.

Herein, in order to induce transient expression of a restriction enzyme gene, first, a nucleic acid construct in the form of, for example, a vector such as a plasmid, in which a restriction enzyme gene can be expressed, is physically-introduced into plant cells using a PEG method, an electroporation method, or a particle gun method. Next, the cells into which the restriction enzyme gene has been introduced are grown in a selection-pressure-free medium.

Accordingly, it is possible to select not only a transformant in which a restriction enzyme gene incorporated into genomic DNA or the like is stably expressed but also a transformant into which a restriction enzyme gene is introduced so as to be merely transiently expressed. In addition, if a nucleic acid construct is physically-introduced into plant cells and the plant cells are continuously grown with the application of selection pressure, a transformant is exclusively selected, in which a restriction enzyme (which is, for example, incorporated into genomic DNA with a selection marker) is stably expressed. In this case, the obtained transformed plant cells cannot survive, and therefore a desired mutant plant cannot be obtained. This is probably because a restriction enzyme gene to be incorporated in genomic DNA often results in a multicopy gene via physical-introduction of a nucleic acid construct such as a particle gun method. The multicopy gene causes an increase in absolute enzyme activity, resulting in highly frequent gene recombination even under normal culture conditions.

In addition, in the case of a PEG method and an electroporation method, a protoplast of a plant cell is obtained by a conventionally known method and then a nucleic acid construct is physically-introduced into the plant cell. Further, in the case of a particle gun method, particles each containing a nucleic acid construct can be embedded in a target plant-derived immature embryo, mature embryo, or callus. Conventionally known methods can be adequately used for preparing an immature embryo, mature embryo, or callus.

In addition, in a case in which a thermophile-derived restriction enzyme gene is introduced into a plant cell, it is preferable to culture the plant cell at a temperature below the temperature at which the restriction enzyme is activated. That is to say, a thermophile-derived restriction enzyme gene is introduced into plant cells and the plant cells are cultured at a temperature below the temperature at which the restriction enzyme is activated. Thus, an unfavorable situation in which plant cells die due to excessively increased levels of restriction enzyme activity can be avoided.

Further, in the above case, it is preferable to treat plant cells at the temperature at which the restriction enzyme is activated before the plant cells are cultured at a temperature below the temperature at which the restriction enzyme is activated. As described above, prior to plant cell culture, the plant cells are treated at a temperature at which the restriction enzyme is activated. Thus, the restriction enzyme activity can be transiently enhanced, promoting gene recombination in the plant cells. Accordingly, a gene recombinant mutant plant can be efficiently produced by treating plant cells at the temperature at which the restriction enzyme is activated prior to plant cell culture. Here, the expression "temperature at which the restriction enzyme is activated" refers to, for example, a temperature from the temperature for plant cell culture (e.g., approximately 32° C.) to the optimum temperature for a restriction enzyme activation. More specifically, such temperature is from the temperature for plant cell culture temperature to 50° C. More preferably, it is from the temperature for plant cell culture to 40° C.

In particular, a technique for inducing transient expression of the above restriction enzyme gene is applied to monocotyledons and preferably rice. A mutant rice having rearranged genomic DNA rearranged as a result of genetic recombination can be produced by such a technique for inducing transient expression of the restriction enzyme gene in rice.

Meanwhile, an example method that can be used as the technique for introducing the restriction enzyme gene into plant cells by the *Agrobacterium* method is the method described in Bechtold, E., Ellis, J. and Pelletier, G. (1993) In Planta *Agrobacterium*-mediated gene transfer by infiltration of adult *Arabidopsis* plants. C. R. Acad. Sci. Paris Sci. Vie, 316, 1194-1199 or the method described in Zyprian E, Kado Cl, *Agrobacterium*-mediated plant transformation by novel mini-T vectors in conjunction with a high-copy vir region helper plasmid, Plant Molecular Biology, 1990, 15 (2), 245-256.

In particular, when a restriction enzyme gene is introduced into a plant cell by the *Agrobacterium* method, the proportion of plant cells killed as a result of restriction enzyme gene introduction can be lowered compared with that obtained when an electroporation method or a particle gun method is used. Therefore, the frequency of genetic recombination of genomic DNA can be increased by introducing a restriction enzyme gene into plant cells by the *Agrobacterium* method, without killing plant cells.

Further, when a restriction enzyme gene is introduced by the *Agrobacterium* method, it is preferable to use, as a promoter that controls the restriction enzyme gene expression, a cauliflower-mosaic-virus-derived 35S promoter or a promoter having a promoter activity lower than that of the cauliflower-mosaic-virus-derived 35S promoter. An example of such promoter having a promoter activity lower than that of the cauliflower-mosaic-virus-derived 35S promoter is a promoter of a gene encoding the *Arabidopsis* sigma factor (AtSIG2).

Furthermore, a method for introducing the above restriction enzyme gene by the *Agrobacterium* method can be applied preferably to a dicotyledon and particularly preferably to *Arabidopsis thaliana*. *Arabidopsis thaliana* mutants having genomic DNA rearranged as a result of genetic recombination can be produced by introducing the restriction enzyme gene into *Arabidopsis thaliana* by the *Agrobacterium* method.

Also, as described above, a mutant plant having rearranged genomic DNA can be obtained by causing redifferentiation of a plant cell or callus, into which a restriction enzyme gene has been introduced, by a conventionally known method.

EXAMPLES

The present invention is hereafter described in greater detail with reference to the following examples, although the technical scope of the present invention is not limited thereto.

Comparative Example 1

Method (1) Preparation of a TaqI Expression Plasmid

A PCR was carried out using, as a template, a budding yeast plasmid (pHS141) (containing His and V5 epitope tags) into which TaqI having the TaqI gene had been cloned and the oligo DNAs described below. Thus, a TaqI gene fragment was obtained.

```
GAGGCGCGCCATGGCCCCTACACAAGCCCA   (SEQ ID NO: 1)
```

(The underlined portion represents an AscI restriction enzyme recognition site.)

```
GCTTAATTAATCAATGGTGATGGTGATGAT   (SEQ ID NO: 2)
```

(The underlined portion represents a PacI restriction enzyme recognition site.)

After confirmation of the sequence of the obtained fragment, the fragment was cleaved with AscI and PacI. The resulting fragment was ligated immediately downstream of the cauliflower mosaic virus 35S promoter (CaMV 35S promoter) such that a p35SP-TaqI plant plasmid having a nopaline synthase gene terminator (Nos ter.) downstream thereof (corresponding to the upper construct in FIG. 1) was constructed. In addition, the V5 tag and His tag recognition sequences are fused to the 3' end of the TaqI gene.

(2) Gene Introduction By A Particle Gun Method

Dehulled seeds were sterilized by shaking with 70% ethanol for 5 minutes and with antiformin (effective chlorine: 5%) for approximately 2 hours. The seeds were washed at least 5 times with sterilized distilled water. The resulting husked rice (brown rice) was inoculated on a callus induction medium (a Linsmaier and Skoog (LS) medium containing 2 mg/L 2,4-dichlorophenoxyacetic acid (2,4-D), 30 g/L sucrose, and 2.8 g/L L-proline) and cultured in a dark place at 28° C. for 5 to 6 days. The scutellum was excised from the rice seed callus and cultured on a mannitol-containing medium (a callus induction medium containing 0.4 M mannitol). Then, scutellum-derived callus of the wet-rice cultivar "Nipponbare" was subjected to gene introduction using a particle gun (BIO-RAD; PDS-1000/He System) in accordance with the method of Ochiai-Fukuda T et al. (2006) (J Biotechnol 122:521-527). In practice, a p35SP-TaqI plasmid and a pAct-gfbsd plasmid having gfbsd obtained by fusing the EGFP (enhanced green fluorescent protein) gene with the blasticidin drug-resistant (blasticidin S deaminase: bsd) gene (corresponding to the lower construct in FIG. 1) (2 µg each) were mixed and allowed to bind to gold particles each having a diameter of 0.6 µm, followed by co-transformation using a particle gun. In addition, gene introduction was carried out using the pAct-gfbsd gene alone to obtain a positive control. After gene introduction, culture was carried out at 28° C. for approximately 24 hours and each culture was applied to a blasticidin S (BS) selection medium (a callus induction medium containing 10 mg/L blasticidin S). During BS selection, calli were formed by culture in plant incubators set at 26° C., 28° C., and 32° C. Subculture in a fresh BS selection medium was carried out approximately every 2 weeks.

Here, the gfbsd gene comprises the EGFP gene and the bsd gene ligated to each other via a spacer sequence consisting of 18 nucleotides in a pAct-gfbsd plasmid, and thus it can cause GFP fluorescence expression and BS (Blasticidin S) resistance expression at the same time. The gfbsd gene was inserted downstream of a rice actin gene promoter (Act1) in a pAct-gfbsd plasmid.

(3) Attempt to Obtain a Stable Transformant

Each callus mass grown on the BS selection medium was observed under a stereoscopic fluorescence microscope (Leica), followed by selection of callus masses emitting GFP fluorescence. A portion of each callus mass was placed on an FTA card (Whatman), covered with parafilm, and strongly pressed with the parafilm, followed by drying. The card was perforated to obtain a disc with a diameter of 2 mm. The disc was washed 3 times with an FTA purified reagent and 2 times with TE, followed by air drying. Each dried disc was subjected to PCR. Then, chromosome transfer into the TaqI gene was confirmed.

For greening and regeneration, each callus mass was applied to a redifferentiation medium (containing 0.2% N-Z amine, 1 mg/L 1-naphthalene acetic acid (NAA), and 2 mg/L 6-benzyl adenine (BA)) and grown at a culture temperature of 26° C. with a light period of 16 hours. Each regenerated greening individual was replanted and subjected to acclimatation treatment under high humidity conditions, with the humidity gradually reduced. Eventually, each individual was grown in a containment greenhouse.

Figure 2:
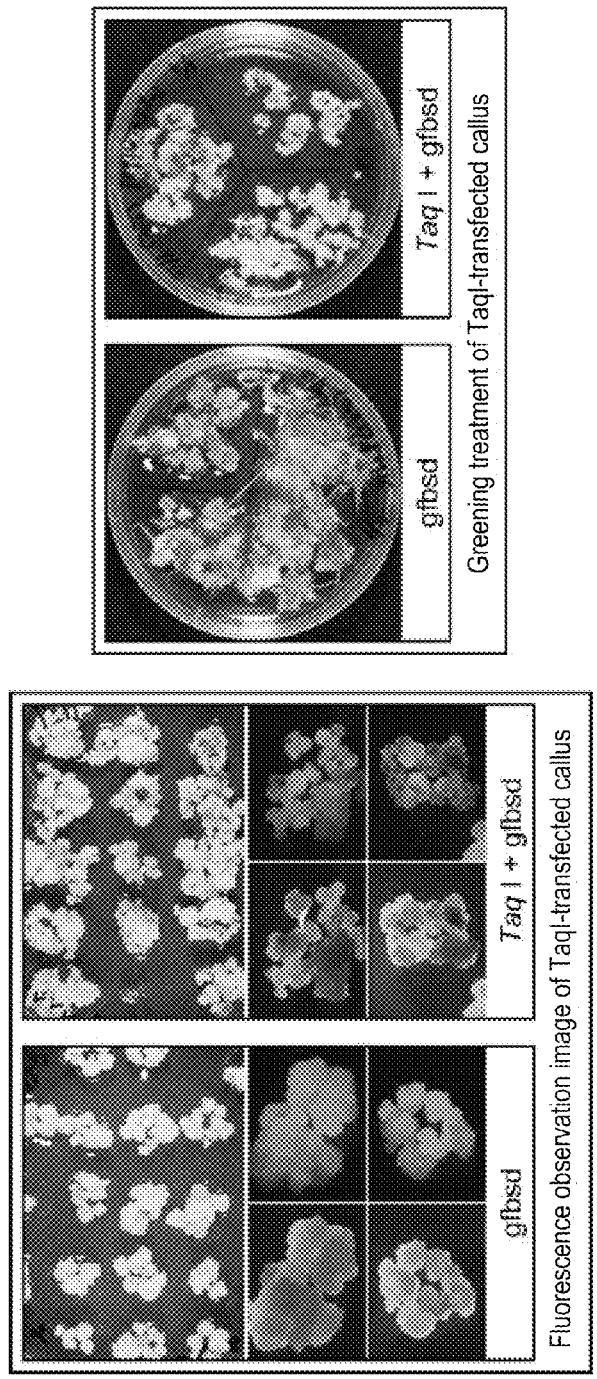
FIG. 2 shows results of observation of fluorescence and results of greening redifferentiation treatment for the transformed rice (callus) produced in Comparative Example 1.

Results (1) As a result of co-transformation of the 35S-promoter-controlled TaqI gene and the fluorescence drug selection marker gfbsd gene into rice-scutellum-derived calli by a particle gun method (FIG. 1), the death of many calli and attenuation of GFP fluorescence were confirmed (FIG. 2).

(2) As a result of examination of temperature conditions (26° C., 28° C., and 32° C.) for BS selection, it was found that the callus growth state deteriorated with temperature increases during selection, resulting in the death of many BS selection calli. In addition, the greening rate of the surviving calli obviously decreased in the subsequent step of greening treatment.

(3) Approximately two thirds of 15 to 20 regenerated rice individuals obtained as a result of successful greening/rooting died during the replanting step. The remaining surviving individuals (⅓) were subjected to RT-PCR for confirmation of gene expression. No TaqI gene expression was confirmed. That is, a rice plant individual in which TaqI functioned was not successfully obtained.

(4) The above results revealed that the use of the TaqI system described in JP Patent No. 4158920 for plant cells under conditions similar to those for yeast transformation causes cell death, making it impossible to produce a mutant plant having recombinant genomic DNA.

Example 1

Method (1) Production of a YFP Recombination Detection Marker

Figure 3:
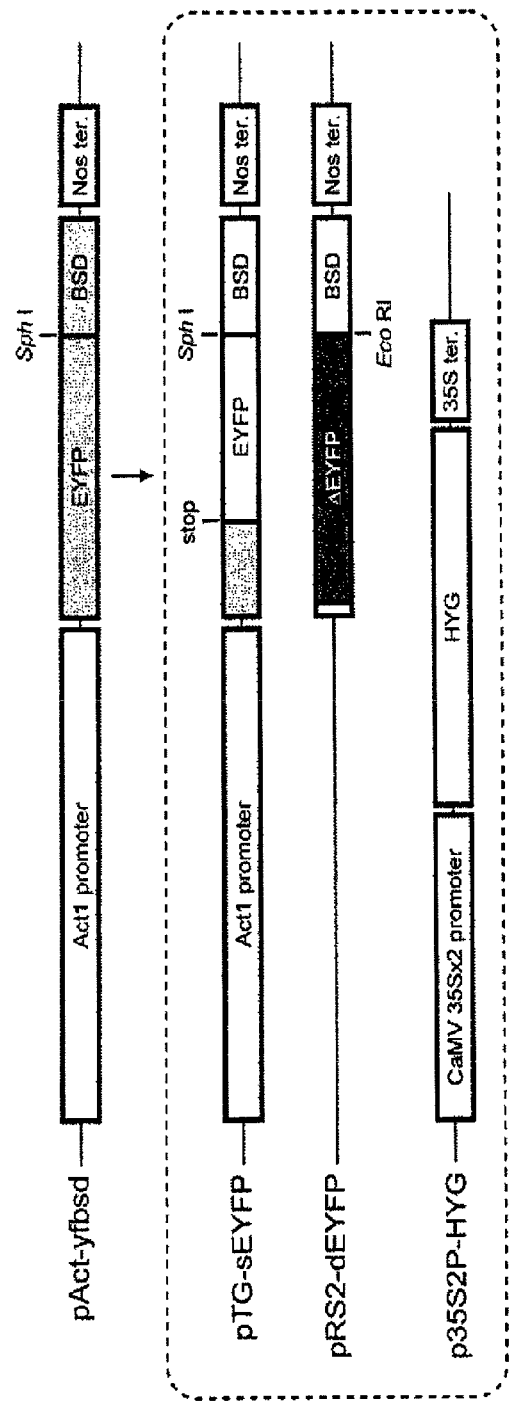
FIG. 3 schematically shows the constructs of the plasmids used in Example 1.

In order to detect the occurrence of homologous DNA recombination, a pAct-yfbsd plasmid (corresponding to the upper construct in FIG. 3) was constructed by ligating the EYFP gene (Clontech) and the bsd gene serving as a fluorescence gene and a drug selection marker gene to each other via a spacer sequence consisting of 6 amino acids (GGG CTC CAC GTG GCC GGC (SEQ ID NO: 26)) and inserting the resultant immediately downstream of an Act1 promoter. A pTG-sEYFP plasmid emitting no YFP fluorescence was constructed by modifying the 114th lysine (AAG) in the EYFP gene region of pAct-yfbsd with a termination codon (TAG) using one-nucleotide substitution, and the plasmid was designated as a receptor marker gene (TG marker) (corresponding to the second construct from the top in FIG. 3). Meanwhile, an EYFP-deficient plasmid (pRS2-dEYFP) (from which the Act1 promoter had been removed) was constructed by deleting 54 nucleotides from the initiation codon of pAct-yfbsd and further editing the SphI restriction enzyme recognition sequence (GCATGC) into the EcoRI restriction enzyme recognition sequence (GAATTC) within the yfbsd sequence, and the plasmid was designated as a donor marker gene (RS marker) (corresponding to the third construct from the top in FIG. 3).

(2) Production of A Callus Containing A YFP Recombination Detection Marker

Three plasmids which were YFP recombination detection marker plasmids (pTG-sEYFP and pRS2-dEYFP) and a plasmid (p35S2P-HYG) having a hygromycin drug-resistant gene (HYG) (shown in a dashed-line frame in FIG. 3) were mixed together (1.5 µg each), followed by co-transformation into a rice scutellum-derived callus by a particle gun method. The callus subjected to transformation was applied to an N6-hygromycin selection medium (an N6 medium containing 2 mg/L 2,4-D, 30 g/L sucrose, 2.8 g/L L-proline, and 50 mg/L hygromycin). The callus was cultured at 28° C. in a plant incubator during hygromycin selection and subcultured in a hygromycin-containing medium approximately every 2 weeks. A portion of each surviving callus mass was placed on an FTA card and immobilized thereon. Chromosome insertion was confirmed for both YFP recombination detection marker plasmids (pTG-sEYFP and pRS2-dEYFP) by PCR. (The callus is hereinafter referred to as a TG/RS callus.)

(3) Introduction of the Restriction Enzyme (TaqI) Gene and Transient Expression

A TG/RS callus was cultured to a mannitol-containing medium, followed by introduction of the restriction enzyme (TaqI) gene (p35SP-TaqI (see Comparative Example 1)) by a particle gun method for induction of transient expression. Each callus mass at 24 hours after gene introduction was cultured to an N6-BS selection medium (an N6 callus induction medium containing 10 mg/L blasticidin S) and cultured at 32° C. for a short time period (3 days).

(4) Detection of Homologous DNA Recombination

Figure 4:
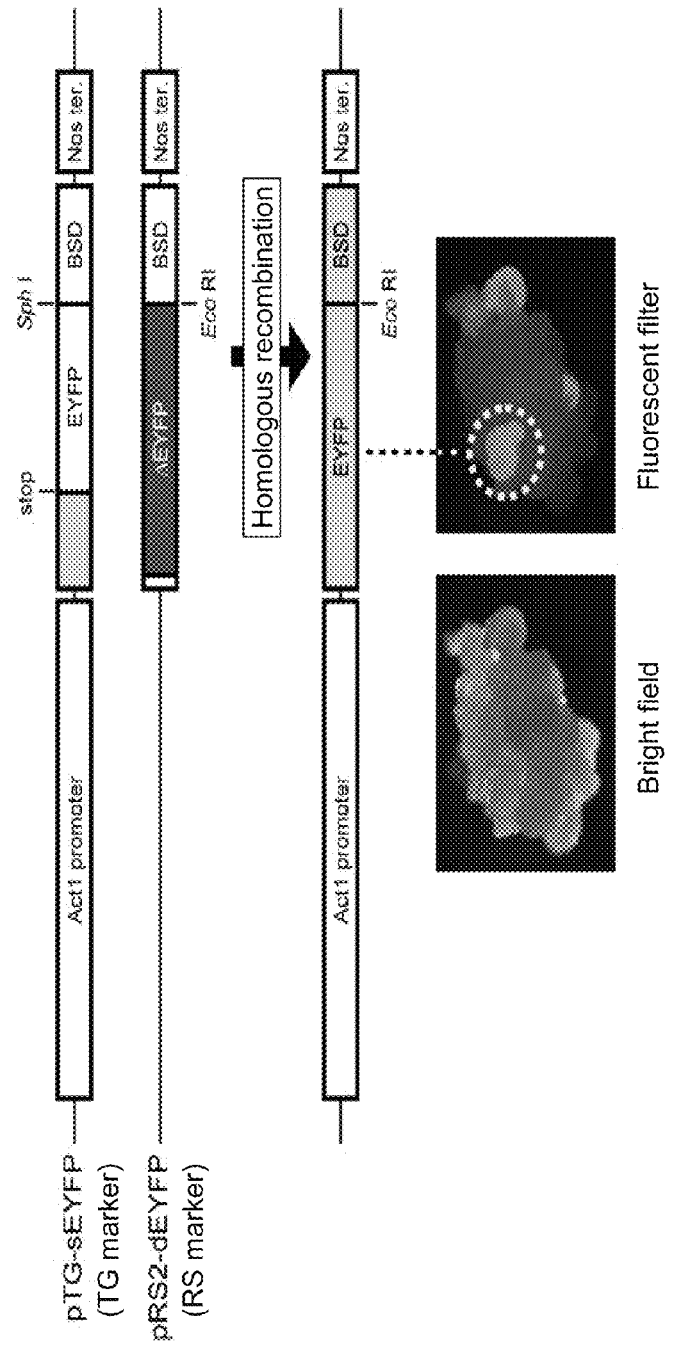
FIG. 4 shows a photo indicating results of observation in a bright field, a photo showing results of observation of fluorescence, and a schematic pattern of homologous recombination for the transformed rice (callus) produced in Example 1.

Each callus mass grown on the N6-BS selection medium was observed in order to observe fluorescence under a stereoscopic fluorescence microscope. YFP fluorescence spots indicating the occurrence of homologous DNA recombination were detected and the number of callus masses having such spots was determined (FIG. 4). It was found that if the transient expression of the TaqI gene described above causes homologous recombination between the TG marker and the RS marker in a TG/RS callus, the YFBSD protein is expressed as shown in FIG. 4. Thus, rice/a callus that emits YFP fluorescence (shown in a dashed-line circle in FIG. 4) is obtained.

Figure 5:
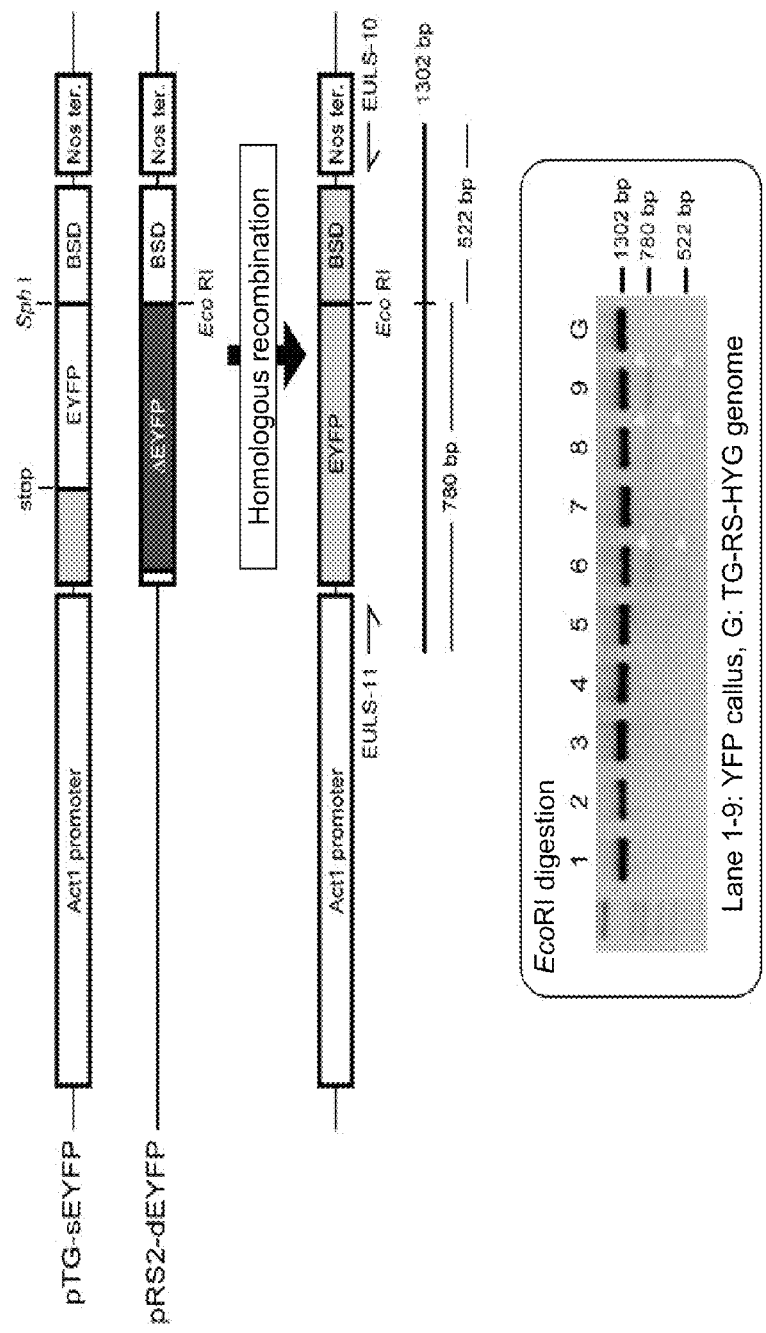
FIG. 5 shows a photo indicating PCR-RFLP analysis results and a schematic pattern of a homologous recombination for the transformed rice (callus) produced in Example 1.

Thereafter, each YFP-fluorescent callus mass was excised in a manner such that it did not contain a nonfluorescent portion. Each callus mass was further finely disrupted and grown on an N6-hygromycin selection medium until callus masses having certain sizes were obtained. Fluorescence emission was observed again under a stereoscopic fluorescence microscope. A callus mass emitting YFP fluorescence alone was obtained, followed by genome extraction using Nucleon PhytoPure (GE Healthcare). PCR was performed using, as a template, the obtained rice genome and oligo DNAs described below. Thus, a gene fragment (1302 nucleotides) corresponding to yfbsd was obtained (FIG. 5).

EULS-11: AGACGATAAGCTTGATATCA    (SEQ ID NO: 3)

(A sequence in the Act1 promoter region)

EULS-10: ACCGGCAACAGGATTCAATC    (SEQ ID NO: 4)

(A sequence in the NosT terminator region)

The fragment obtained by PCR was cleaved with EcoRI and confirmed by electrophoresis (FIG. 5). When a PCR amplification product was cleaved with EcoRI, a DNA fragment having 780 base pairs and a DNA fragment having 522 base pairs were formed, as indicated by arrows in FIG. 5. The occurrence of homologous recombination in the yfbsd gene can be confirmed by detecting these DNA fragments.

(5) Acquisition of A Transformant

The YFP-fluorescent callus mass was cultured to a redifferentiation medium and grown at a culture temperature of 26° C. with a light period of 16 hours. Each greening individual was replanted, subjected to acclimatation treatment, and grown in a containment greenhouse.

Results (1) After the establishment of the TG/RS callus line, introduction of the TaqI gene was carried out by a particle gun method so as to cause transient expression of the gene. As a result, YFP fluorescent spots indicating the occurrence of TaqI-dependent recombination were confirmed to have appeared (FIG. 4). In addition, a callus mass corresponding to the fluorescent spot portion was isolated and grown, followed by genome extraction and PCR-RFLP analysis. As a result, homologous recombination was confirmed to have been activated (FIG. 5).

Figure 6:
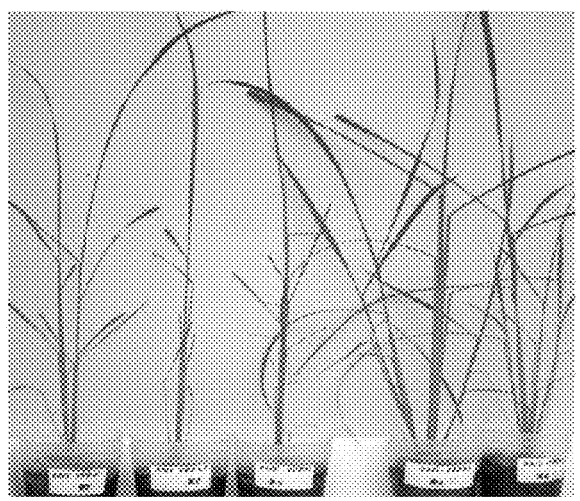
FIG. 6 shows a photo indicating observation results for the transformed rice (plant) produced and redifferentiated in Example 1.

(2) After isolation/acquisition of the YFP fluorescence callus mass, the callus mass was grown to yield rice individuals. Accordingly, mutants exhibiting morphological changes were obtained (FIG. 6). More specifically, individuals with morphological phenotypes such as dwarf lines were obtained at high frequency.

(3) The above results revealed that cell death can be prevented by causing transient expression of TaqI in plant cells and growing the plant cells at a temperature below the temperature at which TaqI is activated (ordinary temperature), thereby inducing genetic recombination of genomic DNA. Accordingly, mutant plants with characteristic changes can be produced.

Example 2

In this Example, experiments of inducing genetic recombination of genomic DNA were carried out in the manner described above with the use of a restriction enzyme other than TaqI, which was used in Example 1.

Method (1) Production of An Sse9I Expression Plasmid

Total DNA synthesis was carried out to optimize the codon use rate of a plant (*Arabidopsis thaliana*) based on the nucleotide sequence information of the Sse9I gene from *Sporosarcina* sp. The nucleotide sequence of the synthesized Sse9I gene is shown in SEQ ID NO: 18. In addition, the totally synthesized Sse9I gene was cloned into pDONR221 (Invitrogen). The obtained vector is referred to as "TCL-AtSse9I/pDONR221."

Next, PCR was performed using TCL-AtSse9I/pDONR221 as a template and the oligo DNAs described below. Thus, an Sse9I gene fragment was obtained.

GA<u>GGCGCGCC</u>ATGGGCATGAACAGCAGATTGTTAA (SEQ ID NO: 19)

(Here, the underlined portion represents an AscI restriction enzyme recognition site.)

GC<u>TTAATTAA</u>TTATTGAGGGAGTGCTTGGGGAGGT (SEQ ID NO: 20)

(Here, the underlined portion represents a PacI restriction enzyme recognition site.)

Figure 7:
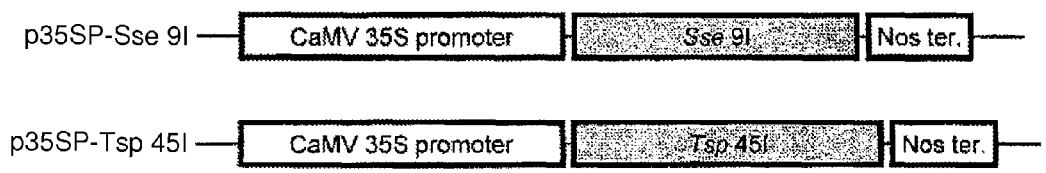
FIG. 7 schematically shows the constructs of the plasmids used in Example 2.

The sequence of the obtained fragment was confirmed, and it was cleaved with AscI and PacI. The resulting fragment was ligated immediately downstream of s cauliflower mosaic virus 35S promoter (CaMV 35S promoter). Thus, a plant plasmid (p35SP-Sse9I) having a nopaline synthase gene terminator (Nos ter.) downstream thereof (corresponding to the upper construct in FIG. 7) was constructed.

(2) Production of A Tsp45I Expression Plasmid

Total DNA synthesis was carried out to optimize the codon use rate of a plant (*Arabidopsis thaliana*) based on the nucleotide sequence information of the Tsp45I gene from *Thermus* sp. YS45. The nucleotide sequence of the synthesized Tsp45I gene is shown in SEQ ID NO: 21. In addition, the totally synthesized Tsp45I gene was cloned into pENTR223.1 (Invitrogen). The obtained vector is referred to as "TCL-AtTSP45I/pENTR223.1_LC."

Next, PCR was performed using TCL-AtTSP45I/pENTR223.1_LC as a template and the oligo DNAs described below. Thus, a Tsp45I gene fragment was obtained.

GA<u>GGCGCGCC</u>ATGGCCGAATGGAACGTTTGGACGC (SEQ ID NO: 22)

(Here, the underlined portion represents an AscI restriction enzyme recognition site.)

GC<u>TTAATTAA</u>TTACAGACCAAGGGCTTCCTCTCCC (SEQ ID NO: 23)

(Here, the underlined portion represents a PacI restriction enzyme recognition site.)

When the nucleotide sequence of the obtained fragment was confirmed, a thymine nucleotide corresponding to the 756th by from the initiation codon was found to have been deleted. Then, a cytosine nucleotide was inserted at the corresponding site using the oligo DNAs described below so as to modify the frame (TT<u>T</u>/Phe→TT<u>C</u>/Phe).

AGGTGAAGTT<u>C</u>CAGAGTGATT (SEQ ID NO: 24)

(Here, the underlined portion represents the modified nucleotide.)

AATCACTCTG<u>G</u>AACTTCACCT (SEQ ID NO: 25)

(Here, the underlined portion represents the modified nucleotide.)

PCR was performed again. The sequence of the obtained fragment was confirmed and cleaved with AscI and PacI. The fragment was ligated immediately downstream of a cauliflower mosaic virus 35S promoter (CaMV 35S promoter) such that a plant plasmid (p35SP-Tsp45I) having a nopaline synthase gene terminator (Nos ter.) (corresponding to the lower construct in FIG. 7) downstream thereof was constructed.

(3) Acquisition of $T_2$ Seeds Containing a YFP Recombination Detection Marker

The 0926-69 line, for which a high YFP fluorescence callus appearance rate had been obtained via introduction of the TaqI gene into a TG/RS callus containing a YFP recombination detection marker plasmid, was cultured to a redifferentiation medium. The line was grown at a culture temperature of 28° C. with a light period of 16 hours. Each regenerated greening individual was replanted and subjected to acclimation treatment under high humidity conditions, with the humidity gradually reduced. Eventually, each individual was grown in a containment greenhouse (0926-69 #3 lines). The obtained $T_1$ seeds were sown and each radicle end was observed using a stereoscopic fluoroscopy to confirm lack of YFP fluorescence emission. Subsequently, each plantlet plant was transplanted to a pot. A leaf portion of each plant was placed on an FTA card and fixed thereon. PCR was performed to confirm that both plasmids (pTG-sEYFP and pRS2-dEYFP) had been inserted into the genome. The individual plants were designated as lines 0926-69 #3-1, #3-2, #3-3, and #3-4. Each plant was grown in a containment greenhouse such that $T_2$ seeds were obtained (hereinafter referred to as "TG/RS($T_2$) seeds").

Figure 8:
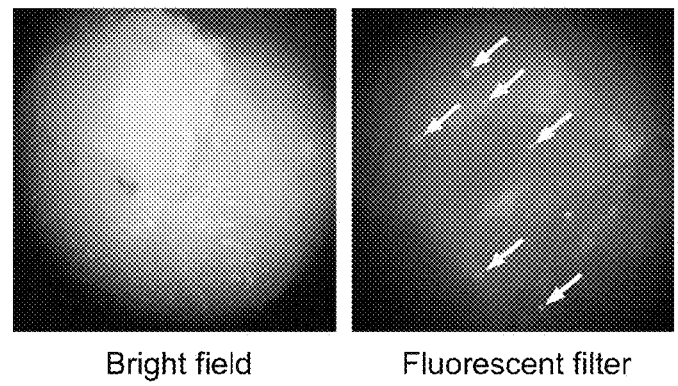
FIG. 8 shows a photo indicating results of observation in a bright field and a photo showing results of observation of fluorescence for the transformed rice (callus) produced in Example 2.
Figure 9:
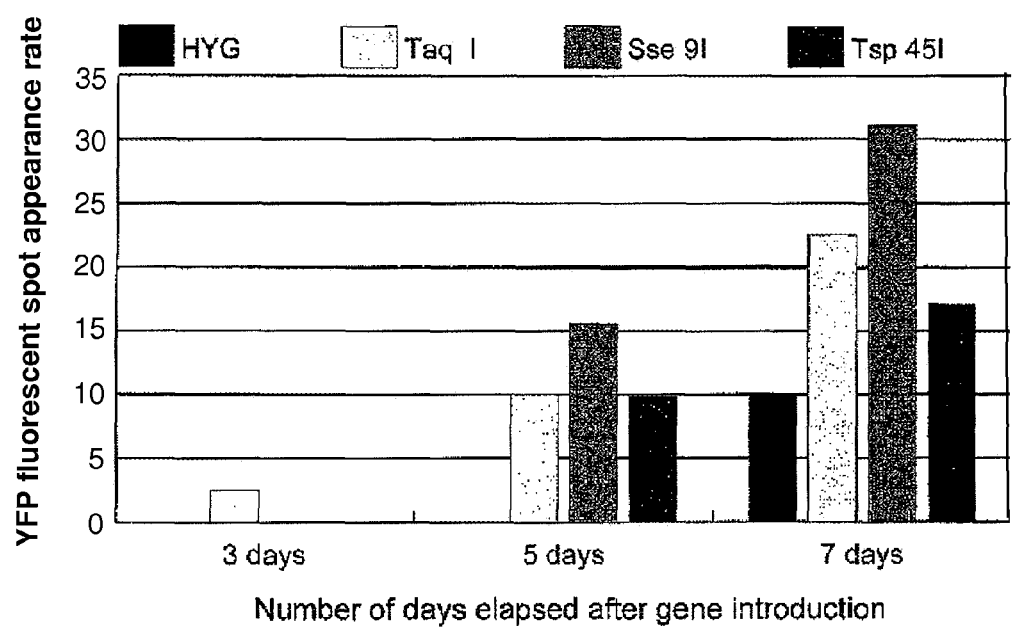
FIG. 9 is a characteristic chart indicating the relationship between the number of days elapsed after gene introduction and the YFP fluorescent spot appearance rate for the transformed rice (callus) produced in Example 2.

(4) Transient Expression of a Restriction Enzyme (Sse9I Or Tsq45I) And the Number of YFP Fluorescent Spots Ripe TG/RS($T_2$) seeds were subjected to callus induction by the method described in (2) in Comparative Example 1. The resulting callus was cultured to a mannitol-containing medium. The gene (p35SP-TaqI, p35SP-Sse9I, or p35SP-Tsp45I) of the restriction enzyme (TaqI, Sse9I, or Tsq45I) or the hygromycin (HYG)-resistant gene (p35S2P-HYG) serving as a negative control was introduced thereinto by a particle gun method, followed by induction of transient gene expression. Each callus mass at 24 hours after gene introduction was cultured to an N6-BS selection medium and cultured at 32° C. Each grown callus mass was observed in order to detect fluorescence under a stereoscopic fluorescence microscope. The number of YFP fluorescence spots indicating the occurrence of DNA homologous recombination (FIG. 8) and the number of callus masses having such spots were determined (FIG. 9). Here, the term "YFP fluorescent spot appearance rate" refers to a value obtained by dividing the number of YFP fluorescent spots appearing on calli by the total number of callus masses obtained by a particle gun method and multiplying the obtained value by 100.

Results

The See9I or Tsp45I gene was introduced by a particle gun method into a callus mass obtained via callus induction from the T2 seeds into which a YFP recombination detection marker (TG/RS/HYG) gene had been introduced and fixed therein so as to cause transient gene expression. Accordingly, the appearance of YFP fluorescent spots was confirmed (FIGS. 8 and 9). Based on the above, it was confirmed that a homologous recombination can be induced even using a restriction enzyme other than TaqI.

Example 3

In this Example, it was demonstrated how the genomic DNA homologous recombination rate would vary as a result of heat treatment following restriction enzyme gene introduction.

Method

Figure 10:
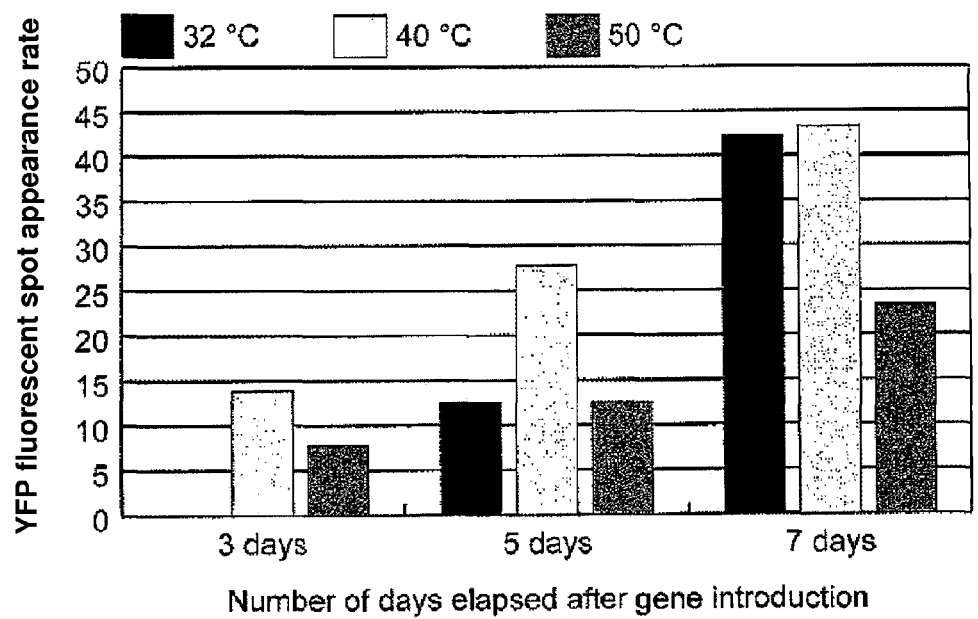
FIG. 10 is a characteristic chart indicating the relationship between the number of days elapsed after gene introduction and the YFP fluorescent spot appearance rate for the transformed rice (callus) produced in Example 3 in a case involving heat treatment (40° C. or 50° C.) and that in a case not involving such heat treatment.

In this Example, the TaqI gene (p35SP-TaqI (see Comparative Example 1)) used in Example 1 was introduced into plant cells, followed by heat treatment. Specifically, in this Example, ripe TG/RS(T2) seeds prepared in Example 2 were subjected to callus induction by the method described in (2) in Comparative Example 1 and then cultured on a mannitol-containing medium. Then, the TaqI gene (p35SP-TaqI) was introduced thereinto by a particle gun method. A callus mass at 24 hours after subjected to gene introduction was sown on an N6-BS selection medium and subjected to heat treatment at 40° C. or 50° C. for 1 hour. The callus mass subjected to heat treatment was grown again at 32° C. Fluorescence emitted from the callus mass in each treatment area was observed at Days 3, 5, and 7 after heat treatment. The number of YFP fluorescence spots indicating the occurrence of DNA homologous recombination and the number of callus masses having such spots were determined (FIG. 10).

Results

The TaqI gene was introduced into a callus mass induced from T2 seeds into which a YFP recombination detection marker (TG/RS/HYG) gene had been introduced and fixed therein by a particle gun method so as to cause transient expression. Then, heat treatment (treatment at 40° C. or 50° C. for 1 hour) was carried out at a temperature at which TaqI is activated. Accordingly, the YFP fluorescent spot appearance rate indicating the occurrence of DNA homologous recombination reached the maximum level in the case of treatment at 40° C. for 1 hour. In this case, the timing of the appearance of the spots was also confirmed early (FIG. 10). Based on the results, it was confirmed that homologous recombination takes place in a relatively early phase after introduction of a restriction enzyme gene and induction of transient expression thereof, followed by treatment at a temperature at which the restriction enzyme is activated. In such case, the frequency of the occurrence of homologous recombination is also improved.

Example 4

1. Materials And Methods 1-1. Experimental Materials

Wild-type *Arabidopsis thaliana* (eco-type Col-0) was used as an experimental plant material. Seeds of the plant were sown in a pot with a diameter of 50 mm containing vermiculite mixed soil and grown in a cultivation room (SANYO) at 22° C. with a light period of 16 hours and a dark period of 8 hours at a light intensity of approximately 30 to 45 μmol/m²/sec.

1-2. Methods 1-2-1. Acquisition of the TaqI Gene

PCR was performed using a budding yeast plasmid (pHS141) having the TaqI gene (JP Patent No. 4158920) as a template and primers described below (BamHI-TaqI-F and TaqI-SacI-R) to which restriction enzyme sites (BamHI and SacI) have been added, respectively, and PrimeSTAR HS DNA Polymerase (Takara Bio Inc.). Regarding a PCR reaction solution composition and reaction conditions, standard protocols attached to the product were referred to.

```
BamHI-TaqI-F (SEQ ID NO: 5):
5'-AGGATCCCCGGGTGGTCAGTCCCTTATGGCCCCTACACA
AGCCCA-3'

TaqI-SacI-R (SEQ ID NO: 6):
5'-AGAGCTCTGTACCTCACGGGCCGGTGAGGGC-3'
```

A PCR amplification product was subjected to agarose gel electrophoresis. Gel containing an object fragment was excised. An object DNA fragment was eluted/purified therefrom using an illustra GFX PCR DNA and Gel Band Purification Kit (GE Healthcare Japan). The obtained DNA fragment was treated using TaKaRa Ex Taq (Takara Bio Inc.) (1U) and dATP (final concentration: 0.2 mM) at 70° C. for 30 min. Then, an adenine nucleotide was added thereto. The DNA fragment to which an adenine nucleotide had been added was ligated to a TA-Cloning pCR2.1 vector with the use of TOPO TA Cloning Kit (Invitrogen) and then transformed into competent cells (ECOSTM Competent *E. coli* DH5α (Nippon Gene Co., Ltd)) included in the kit. After transformation, the resultant was cultured in an LB medium supplemented with 50 μl/ml kanamycin for transformant selection. Appearing colonies were subjected liquid culture in an LB medium supplemented with 50 μl/ml kanamycin. Plasmid DNA was prepared from the obtained cells using a Plasmid Mini Kit (QIAGEN). A vector into which the obtained TaqI gene had been cloned was subjected to a sequence reaction using a BigDye Terminater v3.1 Cycle Sequencing Kit (Applied Biosystems). Then, nucleotide sequence determination was carried out by an Applied Biosystems 3130 Genetic Analyzer (Applied Biosystems). The nucleotide sequence of the TaqI gene-coding region is shown in SEQ ID NO: 7.

1-2-2. Acquisition of the TaqI-NLS Gene

The TaqI-NLS gene in which a nuclear localization signal (NLS) had been added on the C-terminal side of TaqI was obtained in the manner described in 1-2-1. In addition, as a primer containing the NLS sequence, a TaqI-NLS-SacI-R primer described below was used instead of TaqI-SacI-R.

```
TaqI-NLS-SacI-R (SEQ ID NO: 8):
5'-AGAGCTCCCCGGGCTATCCTCCAACCTTTCTCTTCTTCTT
AGGCTGCAGACCTCCCGGGCCGGTGAGGGCTTCC-3'
```

The nucleotide sequence of the TaqI gene-coding region containing the NLS sequence is shown in SEQ ID NO: 9.

1-2-3. Preparation of Genomic DNA

Young leaves were collected from *Arabidopsis thaliana* cultivated in 1-1 and disrupted under liquid nitrogen freezing.

Genomic DNA was prepared using a DNA preparation kit (DNeasy Plant Mini Kit) (QIAGEN) in accordance with standard protocols attached to the kit.

1-2-4. Acquisition of An HSP18.2 Promoter

PCR was performed in the manner described in 1-2-1 using *Arabidopsis thaliana* genomic DNA prepared in 1-2-3 as a template and primers (SalI-HSP18.2-F and HSP18.2-BamHI-R) described below to which restriction enzyme sites (SalI and BamHI) had been added, respectively, in order to amplify the promoter portion (HSP18.2 promoter) of *Arabidopsis thaliana* HEAT SHOCK PROTEIN 18.2 (At5g59720).

```
SalI-HSP18.2-F(SEQ ID NO: 10):
5'-AGTCGACTCTGGTGGTTTCAACTTGGG-3'

HSP18.2-BamHI-R(SEQ ID NO: 11):
5'-AGGATCCTGTTCGTTGCTTTTCGGGAG-3'
```

The PCR amplification product was subjected to cloning in the manner described in 1-2-1 for nucleotide sequence determination. The nucleotide sequence of an HSP18.2 promoter is shown in SEQ ID NO: 12.

1-2-5. Acquisition of An AtSIG2 Promoter

PCR was performed in the manner described in 1-2-1 using *Arabidopsis thaliana* genomic DNA prepared in 1-2-3 as a template and primers (SalI-AtSIG2-F and AtSIG2-BamHI-R) described below to which restriction enzyme sites (SalI and BamHI) had been added, respectively, in order to amplify the promoter portion (AtSIG2 promoter) of *Arabidopsis thaliana* SIG2 (SIGMA SUBUNIT OF CHLOROPLAST RNA POLYMERASE) (At1g08540).

```
SalI-AtSIG2-F(SEQ ID NO: 13):
5'-AGTCGACCGATCTTTCTCCAACAAGCTT-3'

AtSIG2-BamHI-R(SEQ ID NO: 14):
5'-AGGATCCGCTCGTTCTTAGCCTATATTCG-3'
```

The PCR amplification product was subjected to cloning in the manner described in 1-2-1 for nucleotide sequence determination. The nucleotide sequence of an AtSIG2 promoter is shown in SEQ ID NO: 15.

1-2-6. Production of A Promoter Cloning Vector (pBI101N2)

A plant expression vector pBI121 (CLONTECH) was treated with restriction enzymes HindIII and BamHI. Next, oligo nucleotides described below were mixed in equal amounts and allowed to stand still at 96° C. for 10 min and then at room temperature for 2 hours. Then, a ligation reaction was carried out using pBI121 subjected to the above restriction enzyme treatment and a DNA Ligation Kit <Mighty Mix> (Takara Bio Inc.). Thus, a promoter cloning vector pBI101N2 was produced.

```
Linker-F2 (SEQ ID NO: 16):
5'-AGCTTGGCGCGCCTTAATTAAACTAGTCTCGAGGTCGACT-3'

Linker-R2(SEQ ID NO: 17):
5'-CTAGAGTCGACCTCGAGACTAGTTTAATTAAGGCGCGCCA-3'
```

1-2-7. Production of Promoter Cloning Vectors (pBI TaqI and pBI TaqI-NLS)

The TaqI gene obtained in 1-2-1 and the TaqI-NLS gene obtained in 1-2-2 were subcloned into the promoter cloning vector pBI101N2 prepared in 1-2-6. Thus, a promoter cloning vector pBI TaqI and a promoter cloning vector pBI TaqI-NLS were produced.

First, the pCR2.1 vector into which the TaqI gene had been cloned in 1-2-1 was treated with restriction enzymes BamHI and SacI. Next, the promoter cloning vector pBI101N2 produced in 1-2-6 was treated with restriction enzymes BamHI and SacI. These restriction enzyme digestion products were subjected to agarose gel electrophoresis. Gel containing an object fragment was excised. The TaqI gene fragment and the pBI101N2 fragment subjected to restriction enzyme treatment were eluted/purified from the gel using illustra GFX PCR DNA and a Gel Band Purification Kit (GE Healthcare Japan). In order to perform subcloning of the TaqI gene fragment using the pBI101N2 fragment as a vector, a ligation reaction was carried out using a DNA Ligation Kit <Mighty Mix> (Takara Bio Inc.). A reaction solution was added to competent cells (ECOSTM Competent *E. coli* DH5α (Nippon Gene Co., Ltd)), followed by transformation in accordance with protocols included in the kit. The resultant was applied to an LB agar medium containing 50 μg/ml kanamycin, followed by overnight culture. Appearing colonies were subjected to liquid culture with an LB medium containing 50 μg/ml kanamycin. Plasmid DNA was prepared from the obtained cells using a Plasmid Mini Kit (QIAGEN). The obtained promoter cloning vector pBI TaqI into which the TaqI gene fragment had been subcloned was subjected to nucleotide sequence determination and sequence analysis.

A promoter cloning vector pBI TaqI-NLS containing the TaqI-NLS gene obtained in 1-2-2 was produced in the manner described above.

1-2-8. Production of Plant Expression Vectors (pBI 35S:TaqI and pBI 35S:TaqI-NLS)

The TaqI gene obtained in 1-2-1 and the TaqI-NLS gene obtained in 1-2-2 were each subcloned into a plant expression vector pBI121 (containing, as a promoter, a cauliflower mosaic virus (CaMV) 35s promoter). Thus, a plant expression vector pBI 35S:TaqI and a plant expression vector pBI 35S:TaqI-NLS were produced.

The pCR2.1 vector into which the TaqI gene had been cloned in 1-2-1 was treated with restriction enzymes BamHI and SacI. Next, pBI121 was treated with restriction enzymes BamHI and SacI in the manner described above. Then, as in 1-2-7, the obtained plant expression vector pBI 35S:TaqI into which the TaqI gene fragment had been subcloned was subjected to nucleotide sequence determination and sequence analysis.

In addition, a plant expression vector pBI 35S:TaqI-NLS containing the TaqI-NLS gene obtained in 1-2-2 was produced in the manner described above.

1-2-9. Production of Plant Expression Vectors (pBI HSP18.2:TaqI and pBI HSP18.2:TaqI-NLS)

The HSP18.2 promoter obtained in 1-2-4 was subcloned into each of the promoter cloning vectors (pBI TaqI and pBI TaqI-NLS) produced in 1-2-7. Thus, a plant expression vector pBI HSP18.2:TaqI and a plant expression vector pBI HSP18.2:TaqI-NLS were produced.

The pCR2.1 vector into which the HSP18.2 promoter had been subcloned in 1-2-4 was treated with restriction enzymes SalI and BamHI. Next, the promoter cloning vector pBI TaqI produced in 1-2-7 was treated with restriction enzymes SalI and BamHI in the manner described above. Then, as in 1-2-7, the obtained plant expression vector pBI HSP18.2:TaqI into which an HSP18.2 promoter had been subcloned was subjected to nucleotide sequence determination and sequence analysis.

Further, a plant expression vector pBI 35S:TaqI-NLS was produced by subcloning the HSP18.2 promoter obtained in 1-2-4 into the promoter cloning vector pBI TaqI-NLS produced in 1-2-7 in the manner described above.

1-2-10. Production of Plant Expression Vector (pBI AtSIG2:TaqI And pBI AtSIG2:TaqI-NLS)

The AtSIG2 promoter obtained in 1-2-5 was subcloned into each of the promoter cloning vectors (pBI TaqI and pBI TaqI-NLS) produced in 1-2-7. Thus, a plant expression vector pBI AtSIG2:TaqI and a plant expression vector pBI AtSIG2:TaqI-NLS were produced.

The pCR2.1 vector into which the AtSIG2 promoter had been cloned in 1-2-5. was treated with restriction enzymes SalI and BamHI. Next, the promoter cloning vector pBI TaqI produced in 1-2-7 was treated with restriction enzymes SalI and BamHI in the manner described above. Then, as in 1-2-7, the obtained plant expression vector pBI AtSIG2:TaqI into which an AtSIG2 promoter had been subcloned was subjected to nucleotide sequence determination and sequence analysis.

In addition, a plant expression vector pBI AtSIG2:TaqI-NLS was produced by subcloning the AtSIG2 promoter obtained in 1-2-4 into the promoter cloning vector pBI TaqI-NLS obtained in 1-2-7 in the manner described above.

1-2-11. Gene Introduction into *Arabidopsis thaliana* by the *Agrobacterium* Method The plant expression vectors produced in 1-2-8 to 1-2-10 were each introduced into an *Agrobacterium tumefaciens* C58C1 line by an electroporation method (Plant Molecular Biology Manual, Second Edition, B. G. Stanton and A. S. Robbert, Kluwer Acdemic Publishers 1994). Next, *Agrobacterium tumefaciens* into which such plant expression vector was introduced into wild-type *Arabidopsis thaliana* (ecotype Col-0) by the infiltration method of Clough et al. (Steven J. Clough and Andrew F. Bent, 1998, The Plant Journal 16, 735-743).

Transformed *Arabidopsis thaliana* was grown at 22° C. with a light period of 16 hours and a dark period of 8 hours at a light intensity of approximately 30 to 45 μmol/m$^2$/sec. Then, T1 seeds were collected. The collected T1 seeds were aseptically sown on a modified MS agar medium [sucrose: 10 g/l; MES (2-Morpholinoethanesulphonic acid): 0.5 g/L; and agar (for bacterial medium; Wako Pure Chemical Industries, Ltd.): 8 g/L] containing kanamycin (50 mg/L), carbenicillin (100 mg/L), and Benlate T wettable powder 20 (20 mg/L: Sumitomo Chemical Co., Ltd.) and cultured in a plant incubator (Tomy Seiko Co., Ltd.) at 22° C. with a light period of 16 hours and a dark period of 8 hours at a light intensity of approximately 60 to 90 μmol/m$^2$/sec, followed by transformant selection. The selected transformants were replanted for acclimatation and grown at 22° C. with a light period of 16 hours and a dark period of 8 hours at a light intensity of approximately 30 to 45 μmol/m$^2$/sec. Then, T2 seeds were obtained by self-fertilization.

In addition, regarding an MS medium, Murashige, T. et al. (1962) Physiol. Plant., 15, 473-497 is referred to.

2. Results

Figure 11:
FIG. 11 shows a photo indicating results of observation of *Arabidopsis thaliana* (plant) transformed with AtSIG2 TaqI-NLS in Example 4.
Figure 12:
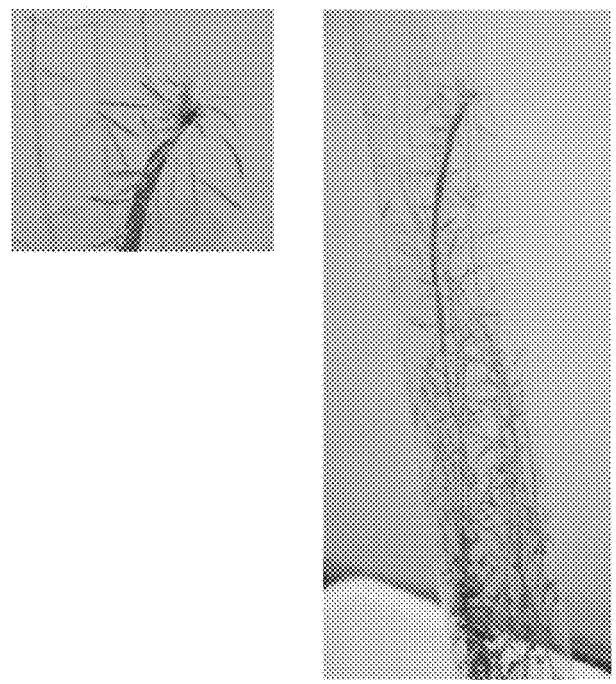
FIG. 12 shows a photo indicating results of observation of *Arabidopsis thaliana* (plant) transformed with AtSIG2 TaqI-NLS in Example 4.
Figure 13:
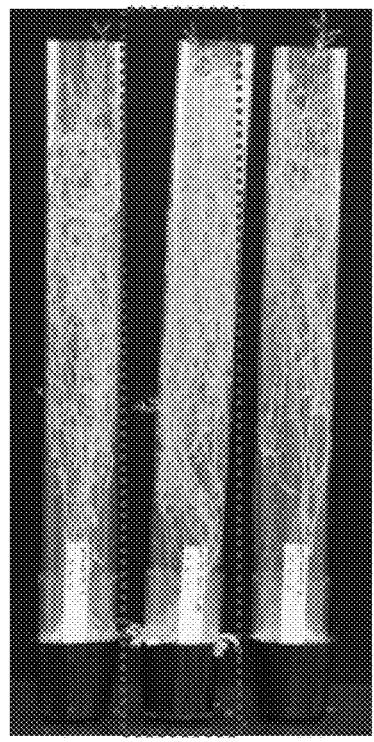
FIG. 13 shows a photo indicating results of observation of *Arabidopsis thaliana* (plant) transformed with pBI 35S:TaqI in Example 4.

FIGS. 11 to 13 show photos of the aerial parts of transformed plants into which the TaqI gene had been introduced, which indicate the results obtained in 1-2-11. In addition, table 1 shows results of transformation efficiency (the number of replanted plants/the number of sown T1 seeds) depending on different promoters.

TABLE 1

| Plant expression vector name | Transformation efficiency | Number of sown T1 seeds | Number of replanted plants |
| --- | --- | --- | --- |
| pBI 35S: TaqI | 0.03% | 55932 | 17 |
| pBI 35S: TaqI-NLS | 0.07% | 63674 | 42 |
| pBI HSP 18.2: TaqI | 0.02% | 52764 | 9 |
| pBI HSP 18.2: TaqI-NLS | 0.01% | 49819 | 5 |
| pBI AtSIG2: TaqI | 0.10% | 48846 | 50 |
| pBI AtSIG2: TaqI-NLS | 0.09% | 60479 | 54 |

Here, FIG. 11 shows a photo of *Arabidopsis thaliana* transformed with a plant expression vector (AtSIG2 TaqI-NLS) obtained with the use of an AtSIG2 promoter and TaqI-NLS in combination. As shown in FIG. 11, the scape of the plant was abnormally branched and continuously grow without dying for 8 months after sowing. In addition, FIG. 12 shows a photo of *Arabidopsis thaliana* transformed with a plant expression vector (AtSIG2 TaqI-NLS) obtained with the use of an AtSIG2 promoter and TaqI-NLS in combination. FIG. 12 shows that the plant has flattened stems. FIG. 13 shows a photo of *Arabidopsis thaliana* transformed with a plant expression vector (pBI 35S:TaqI) obtained with the use of a CaMV 35s promoter and TaqI in combination. As shown in FIG. 13 increased production of in biomass can be confirmed.

The above results revealed that genetic recombination of genomic DNA can be induced by introducing the restriction enzyme TaqI gene into a plant (*Arabidopsis thaliana*) by the *Agrobacterium* method, allowing production of mutant plants having different characteristics. In addition, as shown in table 1, promoters used in combination with TaqI under the cultivation conditions of the present invention are preferably, a CaMV 35s promoter and an AtSIG2 promoter having promoter activity lower than that of the CaMV 35s promoter.

What is claimed is:

1. A method for producing a mutant plant, comprising:
   (a) introducing a DNA construct into a plant cell using an *Agrobacterium*, said DNA construct comprising a promoter operably linked to a polynucleotide encoding a restriction enzyme, wherein said restriction enzyme recognizes a recognition sequence of 4 to 5 nucleotides;
   (b) culturing said plant cell to express said restriction enzyme;
   (c) transiently activating the restriction enzyme in said plant cell, wherein the transient activation of the restriction enzyme induces genetic recombination of the genomic DNA of said plant cell; and
   (d) growing the plant cell, under conditions in which said restriction enzyme is inactive, to produce a mutant plant,
   wherein the transient activation of the restriction enzyme, and the inactivation of the restriction enzyme, are achieved by changing the temperature of said plant cell.

2. The method according to claim 1, wherein the promoter is a cauliflower-mosaic-virus-derived 35S promoter, or is a promoter that, when in said plant cell, is weaker than the cauliflower-mosaic-virus-derived 35S promoter when in said plant cell.

3. The method according to claim 2, wherein the promoter that is weaker than the cauliflower-mosaic-virus-derived 35S promoter is an *Arabidopsis thaliana* SIG2 promoter.

4. A method of increasing the frequency of genetic recombination, comprising:
   (a) introducing a DNA construct into a plant cell using an *Agrobacterium*, said DNA construct comprising a promoter operably linked to a polynucleotide encoding a restriction enzyme, wherein said restriction enzyme recognizes a recognition sequence of 4 to 5 nucleotides;
   (b) culturing said plant cell to express said restriction enzyme;
   (c) transiently activating the restriction enzyme in said plant cell, wherein the transient activation of the restriction enzyme induces genetic recombination of the genomic DNA of said plant cell; and
   (d) growing the plant cell under conditions in which said restriction enzyme is inactive,
   wherein the transient activation of the restriction enzyme, and the inactivation of the restriction enzyme, are achieved by changing the temperature of said plant cell.

5. The method of claim 4, wherein the promoter is a cauliflower-mosaic-virus-derived 35S promoter, or is a promoter that, when in said plant cell, is weaker than the cauliflower-mosaic-virus-derived 35S promoter when in said plant cell.

6. The method of claim 5, wherein the promoter that is weaker than the cauliflower-mosaic-virus-derived 35S promoter is an *Arabidopsis thaliana* SIG2 promoter.

7. A method for producing a mutant plant, comprising:
   (a) introducing a DNA construct into a plant cell using a particle gun, said DNA construct comprising a promoter operably linked to a polynucleotide encoding a restriction enzyme, wherein said restriction enzyme recognizes a recognition sequence of 4 to 5 nucleotides;
   (b) culturing said plant cell to express said restriction enzyme;
   (c) transiently activating the restriction enzyme in said plant cell, wherein the transient activation of the restriction enzyme induces genetic recombination of the genomic DNA of said plant cell; and
   (d) growing the plant cell, under conditions in which said restriction enzyme is inactive, to produce a mutant plant,
   wherein the transient activation of the restriction enzyme, and the inactivation of the restriction enzyme, are achieved by changing the temperature of said plant cell.

8. The method according to claim 7, wherein the promoter is a cauliflower-mosaic-virus-derived 35S promoter, or is a promoter that, when in said plant cell, is weaker than the cauliflower-mosaic-virus-derived 35S promoter when in said plant cell.

9. The method according to claim 8, wherein the promoter that is weaker than the cauliflower-mosaic-virus-derived 35S promoter is an *Arabidopsis thaliana* SIG2 promoter.

10. A method of increasing the frequency of genetic recombination, comprising:
    (a) introducing a DNA construct into a plant cell using a particle gun, said DNA construct comprising a promoter operably linked to a polynucleotide encoding a restriction enzyme, wherein said restriction enzyme recognizes a recognition sequence of 4 to 5 nucleotides;
    (b) culturing said plant cell to express said restriction enzyme;
    (c) transiently activating the restriction enzyme in said plant cell, wherein the transient activation of the restriction enzyme induces genetic recombination of the genomic DNA of said plant cell; and
    (d) growing the plant cell under conditions in which said restriction enzyme is inactive,
    wherein the transient activation of the restriction enzyme, and the inactivation of the restriction enzyme, are achieved by changing the temperature of said plant cell.

11. The method of claim 10, wherein the promoter is a cauliflower-mosaic-virus-derived 35S promoter, or is a promoter that, when in said plant cell, is weaker than the cauliflower-mosaic-virus-derived 35S promoter when in said plant cell.

12. The method of claim 11, wherein the promoter that is weaker than the cauliflower-mosaic-virus-derived 35S promoter is an *Arabidopsis thaliana* SIG2 promoter.

\* \* \* \* \*